United States Patent [19]  
Tronchet et al.

[11] 4,192,868  
[45] Mar. 11, 1980

[54] NOVEL ARYL-HEXAFURANOSIDES AND PROCESSES FOR THEIR PREPARATION

[75] Inventors: Jean M. J. Tronchet, Grilly, France; Bruno Baehler, Troinex, Switzerland; Alberto Rossi, Oberwil, Switzerland; Gerhard Baschang, Bettingen, Switzerland; Alex Sele, Muttenz, Switzerland

[73] Assignee: Ciba-Geigy Corporation, Ardsley, N.Y.

[21] Appl. No.: 880,255

[22] Filed: Feb. 22, 1978

[30] Foreign Application Priority Data

Feb. 25, 1977 [CH] Switzerland ............... 2396/77

[51] Int. Cl.² ................. A61K 31/70; C07H 15/00
[52] U.S. Cl. ............................. 424/180; 536/4
[58] Field of Search ................ 536/4, 1; 424/180

[56] References Cited  
U.S. PATENT DOCUMENTS

| 3,781,267 | 12/1973 | Jaques et al. | 536/4 |
| 3,862,121 | 1/1975 | Jaques et al. | 536/4 |
| 3,978,041 | 8/1976 | Jaeggi et al. | 536/4 |

Primary Examiner—Johnnie R. Brown  
Assistant Examiner—Blondel Hazel  
Attorney, Agent, or Firm—John J. Maitner

[57] ABSTRACT

The invention relates to processes for the preparation of novel aryl-hexafuranosides of the formula

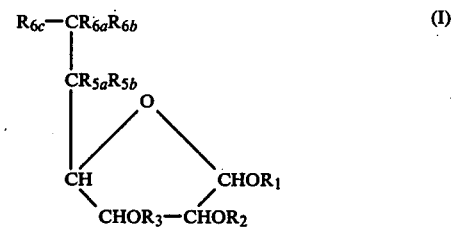

in which $R_1$ is lower alkyl or cycloalkyl and $R_2$ is hydrogen, lower alkyl or acyl, or $R_1$ and $R_2$ together are alkylidene or cycloalkylidene, $R_3$ is hydrogen, lower alkyl, lower alkenyl or aryl-lower alkyl, $R_{5a}$ and $R_{6a}$ independently of one another are hydrogen or lower alkyl, $R_{5b}$ and $R_{6b}$ independently of one another are hydrogen, hydroxyl, lower alkoxy or amino, or $R_{5b}$ and $R_{6b}$ together are a C—C bond, epoxy or lower alkylidene, and $R_{6c}$ is aryl, by methods known per se.

These novel compounds have an anti-inflammatory and/or antinociceptive action.

42 Claims, No Drawings

NOVEL ARYL-HEXAFURANOSIDES AND PROCESSES FOR THEIR PREPARATION

The invention relates to novel aryl-hexafuranosides of the formula I

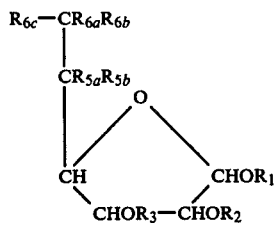

in which $R_1$ is lower alkyl or cycloalkyl and $R_2$ is hydrogen, lower alkyl or acyl, or $R_1$ and $R_2$ together are alkylidene or cycloalkylidene, $R_3$ is hydrogen, lower alkyl, lower alkenyl or aryl-lower alkyl, $R_{5a}$ and $R_{6a}$ independently of one another are hydrogen or lower alkyl, $R_{5b}$ and $R_{6b}$ independently of one another are hydrogen, hydroxyl, lower alkoxy or amino, or $R_{5b}$ and $R_{6b}$ together are a C—C bond, epoxy or lower alkylidene, and $R_{6c}$ is aryl, and processes for their preparation.

In the preceding and following text, lower radicals are especially those having not more than 7 C atoms and in particular having not more than 4 C atoms.

The novel hexafuranosides of the formula I are in particular xylohexafuranosides, i.e. hexafuranosides of the formula

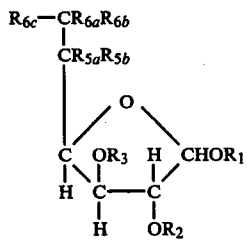

Lower alkyl $R_1$, $R_2$, $R_3$, $R_{5a}$ and $R_{6a}$ is, for example, isopropyl or straight-chain or branched butyl, pentyl, hexyl or heptyl bonded in any position, and in particular methyl, ethyl or n-propyl.

Cycloalkyl $R_1$ is especially cycloalkyl having 3-10 ring members and in particular having 3-8 ring members and having not more than 12 C atoms and in particular having not more than 8 C atoms, such as cyclopropyl, cyclobutyl, cycloheptyl, cyclooctyl and especially cyclopentyl or cyclohexyl, and these radicals can also be lower alkylated, especially mono-lower alkylated, such as methylated, for example methyl-cyclopentyl or methyl-cyclohexyl, such as 2-methyl-cyclopentyl or 3-methyl-cyclohexyl.

Alkylidene formed by $R_1$ and $R_2$ together is especially alkylidene having not more than 7, and preferably not more than 4, C atoms, such as methylene, ethylidene, n-propylidene, n-butylidene and in particular isopropylidene. These radicals can also be substituted, for example by hydroxyl, lower alkoxy, such as methoxy or ethoxy, or halogen, such as chlorine or bromine, or by methyl which is unsubstituted or substituted by lower alkyl, lower alkoxy, hydroxyl or halogen.

Cycloalkylidene, which can be formed by $R_1$ and $R_2$ together, is especially cycloalkylidene having 4 to 7 C atoms and preferably having 5 or 6 C atoms, such as cyclopentylidene or cyclohexylidene.

Acyl $R_2$ is especially an acyl radical of an organic acid, especially of an organic carboxylic acid. Thus, acyl is especially alkanoyl, in particular lower alkanoyl, such as acetyl or propionyl, carboxy-alkanoyl, in particular carboxy-lower alkanoyl, such as succinyl or malonyl, or aroyl, such as 1-naphthoyl or 2-naphthoyl and especially benzoyl or benzoyl substituted by halogen, lower alkyl, lower alkoxy, trifluoromethyl, hydroxy or lower alkanoyloxy, such as salicyloyl or acetylsalicyloyl, and also pyridylcarbonyl, for example nicotinoyl.

Acyl $R_2$ is, however, also an acyl radical of a carboxylic acid having an anti-inflammatory action, especially an acyl radical of the formula II

in which $R_7$ is a hydrogen atom or a lower alkyl radical, especially a methyl radical, and Ar is a phenyl or naphthyl radical, which preferably can be substituted by cycloalkyl, cycloalkenyl, aryl, lower alkyl, lower alkoxy, phenoxy, halogen, pyrrolino and/or hydroxyl groups.

Cycloalkyl, as a substituent of the phenyl radical Ar, is, for example, monocyclic, bicyclic or polycyclic cycloalkyl having, for example, not more than 12, such as 3-8 and preferably 5-8, ring carbon atoms, especially cyclopentyl or cyclohexyl.

Cycloalkenyl, as a substituent of the phenyl radical Ar, is, for example, a monocyclic cycloalkenyl having 3-8 and preferably 5-8 ring carbon atoms, especially cyclohexenyl or cyclopentenyl.

Lower alkyl, as a substituent of the radical Ar, is especially the abovementioned lower alkyl, in particular methyl.

Lower alkenyl $R_3$ is, for example, isopropenyl, 2-methallyl, 3-butenyl and in particular allyl. Aryl-lower alkyl $R_3$ is especially aryl-lower alkyl in which the lower alkyl moiety is in particular as defined above and especially methyl, and in which the aryl moiety is naphthyl or in particular phenyl, which can be substituted, such as by halogen, lower alkyl, lower alkoxy, trifluoromethyl and/or hydroxyl, the aryl moiety carrying several, such as two or three, substituents, but especially only one substituent, preferably in the 4-position, or being unsubstituted.

Lower alkoxy in the above radicals or as radicals $R_{5b}$ and $R_{6b}$ is especially lower alkoxy in which the lower alkyl moiety is as defined for $R_2$, such as ethoxy, n-propoxy, iso-propoxy or in particular methoxy.

Amino $R_{5b}$ or $R_{6b}$ is, for example, free amino, lower alkylamino, di-lower alkylamino or lower alkyleneamino and these radicals are in particular as defined above.

Lower alkylidene, which is formed by $R_{5b}$ and $R_{6b}$ together, is especially lower alkylidene having not more than 7 and preferably not more than 4 C atoms, such as ethylidene, n-propylidene, iso-propylidene, n-butylidene and in particular methylene, and the alkylidene radicals can also be substituted, such as by halogen, for example chlorine or bromine. Substituted alkylidene is especially monosubstituted or disubstituted lower alkylidene, such as the abovementioned radicals with one or two chlorine atoms or bromine atoms, and in particular chloromethylene, dichloromethylene, bromomethylene or dibromomethylene.

Aryl $R_{6c}$ is polynuclear or especially mononuclear aryl, such as naphthyl, for example 1- or 2-naphthyl, diphenyl or especially phenyl, and the aryl radicals can also be substituted, such as by halogen, for example chlorine or bromine, trifluoromethyl, lower alkyl, such as the lower alkyl mentioned for $R_2$, lower alkoxy, such as the abovementioned lower alkoxy, cyano, nitro, amino, lower alkylamino or di-lower alkylamino, in which lower alkyl is as defined for $R_2$, such as ethylamino, diethylamino, N-methyl-N-ethylamino or especially methylamino or dimethylamino. Aryl $R_{6c}$ is, for example, disubstituted or trisubstituted, preferably monosubstituted and very particularly unsubstituted.

The novel compounds have valuable pharmacological properties.

Thus, the hexafuranosides according to the invention have an anti-inflammatory action, as can be shown in animal experiments, for example on local epicutaneous administration in concentrations of about 100–300 mg/ml to mice in the croton oil oedema test (Experientia 24, 581 (1968)), and also an in vitro antagonism towards histamine, arachidonic acid peroxide and wasp stings, as can be shown on isolated guinea pig intestines, in concentrations of about 1–10 μg/ml (Schweiz. med. Wochenschrift 97, 553 (1967)). The novel hexafuranosides can therefore be used as compounds having an anti-inflammatory action, for example for the treatment of inflammations of a rheumatic nature.

The novel compounds which contain, as the substituent $R_2$ (formula I), an acyl radical of a carboxylic acid having an anti-inflammatory action also show novel antinociceptive (analgesic) actions coupled with low toxicity. Furthermore, a pronounced analgesic component can be determined with the aid of the benzoquinone writhing syndrome test [based on the test method described by Siegmund et al., Proc. Soc. Exptl. Biol. Med., volume 95, page 729–733 (1957)] on oral administration in doses of about 0.1 g/kg to about 0.3 g/kg to mice. These novel compounds can therefore be used as compounds having an anti-inflammatory (antiphlogistic), for example anti-exudative or vascular permeability-inhibiting action, in particular as compounds having an analgesic action, especially for the treatment of painful symptoms of a rheumatic nature.

Compounds which are particularly suitable because of their anti-inflammatory action are those of the formula I in which $R_1$ is lower alkyl, $R_2$ is an acyl radical of a carboxylic acid having an anti-inflammatory action, $R_3$ is hydrogen, lower alkyl, lower alkenyl, benzyl, lower alkyl-benzyl, lower alkoxybenzyl, halogenobenzyl or trifluoromethylbenzyl, $R_{5a}$ and $R_{6a}$ independently of one another are hydrogen or lower alkyl and $R_{5b}$ and $R_{6b}$ independently of one another are hydrogen, hydroxyl or lower alkoxy or lower alkylamino, or $R_{5b}$ and $R_{6b}$ together are a C—C bond, epoxy, lower alkylidene or halogeno-lower alkylidene, and $R_{6c}$ is phenyl, halogenophenyl, trifluoromethylphenyl, lower alkylphenyl or lower alkoxy-phenyl.

Amongst these compounds, particularly preferred compounds are those in which $R_1$ is lower alkyl, $R_2$ is an acyl radical of the formula III

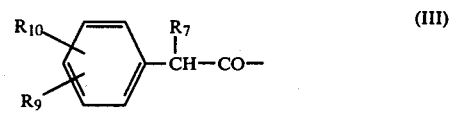

in which $R_7$ is a hydrogen atom or preferably a lower alkyl radical, $R_9$ is a hydrogen atom, a halogen atom or a trifluoromethyl group and $R_{10}$ in particular is a phenyl radical, but especially a 5-membered to 8-membered cycloalkyl radical with preferably one double bond, preferably in the $\Delta^1$-position, in the ring, and less preferentially a lower alkoxy radical or a preferably branched lower alkyl radical, and also a 1-pyrrolyl radical, and $R_3$, $R_{5a}$, $R_{5b}$, $R_{6a}$, $R_{6b}$ and $R_{6c}$ are as defined above.

Preferred compounds are those in which $R_1$ is lower alkyl, $R_2$ is an acyl radical of the formula III, in which $R_7$ is lower alkyl, $R_9$ is hydrogen or chlorine and $R_{10}$ is phenyl, cyclopentyl, cyclohexyl, 1-cyclopentenyl, 1-cyclohexenyl, 1-cycloheptenyl, 1-cyclooctenyl, isopropyl, 1-methyl-n-propyl-1- or $\Delta^3$-pyrrolinyl, and $R_3$ is lower alkyl, benzyl, methylbenzyl, methoxybenzyl, chlorobenzyl, bromobenzyl or trifluoromethylbenzyl, $R_{5a}$ and $R_{6a}$ are hydrogen and $R_{5b}$ and $R_{6b}$ independently of one another are hydrogen, hydroxyl, lower alkoxy or lower alkylamino, or $R_{5b}$ and $R_{6b}$ together are a C—C bond, epoxy, methylene, chloromethylene, dichloromethylene, bromomethylene or dibromomethylene, and $R_{6c}$ is phenyl, chlorophenyl, bromophenyl, trifluoromethylphenyl, methylphenyl or methoxyphenyl.

Particularly preferred compounds are those in which $R_1$ is straight-chain $C_1$-$C_4$-lower alkyl, $R_2$ is an acyl radical of the formula III, in which $R_7$ is methyl, $R_9$ is hydrogen and $R_{10}$ is phenyl, cyclohexyl, 1-cyclohexenyl, 1-cycloheptenyl, 1-cyclooctenyl or $\Delta^3$-pyrrolinyl, $R_3$ is methyl, ethyl, n-propyl, n-butyl, benzyl, methylbenzyl, methoxybenzyl, chlorobenzyl, bromobenzyl or trifluoromethylbenzyl, $R_{5a}$ and $R_{6a}$ are hydrogen and $R_{5b}$ and $R_{6b}$ independently of one another are hydrogen, hydroxyl, methoxy or isopropylamino, or $R_{5b}$ and $R_{6b}$ together are a C—C bond, epoxy, methylene, chloromethylene or dichloromethylene, and $R_{6c}$ is phenyl, chlorophenyl, bromophenyl, trifluoromethylphenyl, methylphenyl or methoxyphenyl.

Very particularly suitable compounds are those in which $R_1$ is methyl, ethyl, n-propyl or n-butyl, $R_2$ is an acyl radical of the formula III, in which $R_7$ is methyl, $R_9$ is hydrogen and $R_{10}$ is phenyl, cyclohexyl, 1-cyclohexenyl, 1-cycloheptenyl, 1-cyclooctenyl or $\Delta^3$-pyrrolinyl, $R_3$ is methyl, ethyl, n-propyl, benzyl or chlorobenzyl, $R_{5a}$ and $R_{6a}$ are hydrogen and $R_{5b}$ and $R_{6b}$ independently of one another are hydrogen, hydroxyl, methoxy or isopropylamino, or $R_{5b}$ and $R_{6b}$ together are a C—C bond, epoxy, methylene, chloromethylene or dichloromethylene, and $R_{6c}$ is phenyl or chlorophenyl.

Preferably, in all the abovementioned ranges of compounds, $R_{5b}$ and $R_{6b}$ together are a C—C bond, and corresponding compounds preferably contain a cis-C—C double bond.

Preferably, in all the abovementioned ranges of compounds, substituted phenyl radicals, including those in benzyl radicals, are substituted in the 4-position (for example $R_{10}$).

Compounds which are particularly preferred because of their anti-inflammatory action are those of the formula I in which $R_1$ is lower alkyl and $R_2$ is hydrogen, lower alkyl, lower alkanoyl, carboxy-lower alkanoyl or aroyl or $R_1$ and $R_2$ together are also lower alkylidene, $R_3$ is hydrogen, lower alkenyl, benzyl, lower alkyl-benzyl, lower alkoxy-benzyl, halogenobenzyl or trifluoromethylbenzyl, $R_{5a}$ and $R_{6a}$ independently of one another are hydrogen or lower alkyl and $R_{5b}$ and $R_{6b}$ independently of one another are hydrogen, hydroxyl, lower alkoxy or lower alkylamino, or $R_{5b}$ and $R_{6b}$ together are a C—C bond, epoxy, lower alkylidene or halogeno-lower alkylidene, and $R_{6c}$ is phenyl, halogenophenyl, trifluoromethylphenyl, lower alkylphenyl or lower alkoxy-phenyl or diphenyl.

Amongst these compounds, particularly preferred compounds are those in which $R_1$ is lower alkyl and $R_2$ is hydrogen, lower alkyl, lower alkanoyl, carboxy-lower alkanoyl, benzoyl, halogenobenzoyl, trifluoromethylbenzoyl, lower alkyl-benzoyl, lower alkoxy-benzoyl, hydroxybenzoyl, lower alkanoyloxybenzoyl or pyridylcarbonyl, or $R_1$ and $R_2$ are lower alkylidene, $R_3$ is hydrogen, lower alkyl, lower alkenyl, benzyl, lower alkyl-benzyl, lower alkoxy-benzyl, halogenobenzyl or trifluoromethylbenzyl, $R_{5a}$ and $R_{6a}$ independently of one another are hydrogen or lower alkyl and $R_{5b}$ and $R_{6b}$ independently of one another are hydrogen, hydroxyl, lower alkoxy or lower alkylamino, or $R_{5b}$ and $R_{6b}$ together are a C—C bond, epoxy, lower alkylidene or halogeno-lower alkylidene, and $R_{6c}$ is phenyl, halogenophenyl, trifluoromethylphenyl, lower alkyl-phenyl or lower alkoxy-phenyl or diphenyl.

Preferred compounds of the formula I are those in which $R_1$ is lower alkyl and $R_2$ is hydrogen, lower alkyl, lower alkanoyl, carboxy-lower alkanoyl, benzoyl, halogenobenzoyl, trifluoromethylbenzoyl, lower alkyl-benzoyl, lower alkoxy-benzoyl, hydroxybenzoyl, lower alkanoyloxy-benzoyl or pyridylcarbonyl, or $R_1$ and $R_2$ together are also lower alkylidene, $R_3$ is lower alkyl, benzyl, methylbenzyl, methoxybenzyl, chlorobenzyl, bromobenzyl or trifluoromethylbenzyl, $R_{5a}$ and $R_{6a}$ are hydrogen and $R_{5b}$ and $R_{6b}$ independently of one another are hydrogen, hydroxyl, lower alkoxy or lower alkylamino, or $R_{5b}$ and $R_{6b}$ together are a C—C bond, epoxy, methylene, chloromethylene, dichloromethylene, bromomethylene or dibromomethylene, and $R_{6c}$ is phenyl, chlorophenyl, bromophenyl, trifluoromethylphenyl, methylphenyl, methoxyphenyl or diphenyl.

Particularly preferred compounds of the formula I are those in which $R_1$ is methyl, ethyl, n-propyl or n-butyl and $R_2$ is hydrogen, methyl, ethyl, n-propyl, n-butyl, lower alkanoyl having 2–4 C atoms, carboxy-lower alkanoyl having 2–4 C atoms, benzoyl, chlorobenzoyl, bromobenzoyl, methylbenzoyl, methoxybenzoyl, hydroxybenzoyl, lower alkanoyloxy-benzoyl having 2–4 C atoms in the lower alkanoyloxy moiety, or pyridylcarbonyl, or $R_1$ and $R_2$ together are also iso-propylidene, $R_3$ is methyl, ethyl, n-propyl, n-butyl, benzyl, methylbenzyl, methoxybenzyl, chlorobenzyl, bromobenzyl or trifluoromethylbenzyl, $R_{5a}$ and $R_{6a}$ are hydrogen and $R_{5b}$ and $R_{6b}$ independently of one another are hydrogen, hydroxyl, methoxy or isopropylamino, or $R_{5b}$ and $R_{6b}$ together are a C—C bond, epoxy, methylene, chloromethylene or dichloromethylene, and $R_{6c}$ is phenyl, chlorophenyl, bromophenyl, trifluoromethylphenyl, methylphenyl, methoxyphenyl or diphenyl.

Very particularly suitable compounds of the formula I are those in which $R_1$ is methyl, ethyl, n-propyl or n-butyl and $R_2$ is hydrogen, methyl, ethyl, n-propyl, acetyl, propionyl, butyryl, benzoyl, chlorobenzoyl, hydroxybenzoyl, acetoxybenzoyl, propionyloxybenzoyl, butyryloxybenzoyl or pyridylcarbonyl, or $R_1$ and $R_2$ together are iso-propylidene, $R_3$ is methyl, ethyl, n-propyl, benzyl or chlorobenzyl, $R_{5a}$ and $R_{6a}$ are hydrogen and $R_{5b}$ and $R_{6b}$ independently of one another are hydrogen, hydroxyl, methoxy or isopropylamino, or $R_{5b}$ and $R_{6b}$ together are a C—C bond, epoxy, methylene, chloromethylene or dichloromethylene, and $R_{6c}$ is phenyl, chlorophenyl or diphenyl.

Preferably, in all the abovementioned ranges of compounds, $R_{5b}$ and $R_{6b}$ together are a C—C bond, and corresponding compounds preferably contain a cis-C—C double bond.

Preferably, in all the abovementioned ranges of compounds, substituted phenyl radicals, including those in benzyl radicals, are substituted in the 4-position.

Preferably, in all the abovementioned ranges of compounds, substituted benzoyl radicals are substituted in the 2-position.

Particularly preferred compounds of the formula I are those in which $R_1$ is methyl, ethyl, n-propyl or n-butyl and $R_2$ is hydrogen, methyl, ethyl, n-propyl, acetyl, propionyl, benzoyl, o-chlorobenzoyl, o-hydroxybenzoyl, o-acetoxybenzoyl, o-propionyloxybenzoyl or pyridylcarbonyl, or $R_1$ and $R_2$ together are isopropylidene, $R_3$ is methyl, ethyl, n-propyl, benzyl or 4-chlorobenzyl, $R_{5a}$ and $R_{6a}$ are hydrogen, $R_{5b}$ and $R_{6b}$ together are a C—C bond and $R_{6c}$ is phenyl, 4-chlorophenyl or diphenyl.

Particularly preferred compounds are those mentioned in the examples.

The novel hexafuranosides are prepared by methods known per se.

Thus, the novel hexafuranosides are obtained when a compound of the formula IV

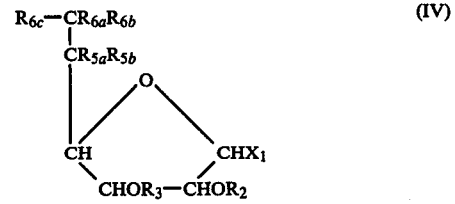

in which $R_2$, $R_3$, $R_{5a}$, $R_{5b}$, $R_{6a}$, $R_{6b}$ and $R_{6c}$ are as defined above, is reacted with a compound $X_2$-$R_1$, in which $R_1$ is as defined above and one of the radicals $X_1$ and $X_2$ is hydroxyl and the other is free or esterified hydroxyl, and $X_1$ and $OR_2$ together can also be an ylidene radical.

Esterified hydroxyl $X_1$ or $X_2$ is, for example, acyloxy, in which acyl is the radical of a carboxylic acid. Thus acyl is, for example, lower alkanoyl, such as acetyl, or aroyl, such as benzoyl.

If one of the radicals $X_1$ and $X_2$ is acyloxy, the reaction is carried out in particular in the presence of an acid, such as a mineral acid, for example a hydrogen halide acid, such as hydrochloric acid.

Esterified hydroxyl $X_1$ or $X_2$ is in particular also reactive esterified hydroxyl.

Reactive esterified hydroxyl $X_1$ or $X_2$ is especially hydroxyl which is esterified with a strong inorganic or organic acid, such as in particular with a hydrogen halide acid, for example hydrochloric acid, hydrobromic acid or hydriodic acid, or with sulphuric acid, or with an organic sulphonic acid, such as with an aromatic or aliphatic sulphonic acid, for example benzenesulphonic acid, 4-bromobenzenesulphonic acid, 4-toluenesulphonic acid or a lower alkanesulphonic acid, for example methanesulphonic acid or ethanesulphonic acid. Thus, reactive esterified hydroxyl $X_1$ or $X_2$ is especially chlorine, bromine, iodine, benzenesulphonyloxy, 4-bromobenzenesulphonyloxy, 4-toluenesulphonyloxy, methanesulphonyloxy or ethanesulphonyloxy.

If $X_1$ is hydroxyl and $X_2$ is reactive esterified hydroxyl, the reaction is advantageously carried out in the presence of a basic agent, such as an alkali metal hydroxide, for example sodium hydroxide or potassium hydroxide, an alkali metal carbonate, such as sodium carbonate or potassium carbonate, or an alkali metal bicarbonate, such as sodium bicarbonate or potassium bicarbonate, or such as a tertiary amine, such as a tri-lower alkylamine, for example triethylamine, or in the presence of silver oxide.

If $X_1$ is reactive esterified hydroxyl and $X_2$ is hydroxyl, the reaction is advantageously carried out in the presence of a basic agent, such as one of those mentioned above, or the alcohol $HOR_1$ is used in the form of a metal salt, for example an alkali metal salt, such as the sodium salt or potassium salt. If appropriate, an acid-binding agent is used, such as a silver, lead or mercury salt or a corresponding oxide, for example silver nitrate, lead-IV chloride, mercury-II chloride, silver oxide, lead-IV oxide or mercury-II oxide.

If $X_1$ is hydroxyl and $X_2$ is hydroxyl, the reaction is advantageously carried out in the presence of an acid. Examples of suitable acids are mineral acids, such as hydrogen halide acids, for example hydrochloric acid, or organic carboxylic acids, such as lower alkanecarboxylic acids, for example acetic acid, or sulphonic acids, such as arylsulphonic acids, for example benzenesulphonic acid or p-toluenesulphonic acid, or mixtures of acids, such as lower alkanecarboxylic acids together with hydrogen halide acids or sulphonic acids, for example acetic acid with hydrochloric acid or with p-toluenesulphonic acid.

Furthermore, the novel hexafuranosides of the formula I in which $R_1$, $R_2$, $R_3$, $R_{5a}$ and $R_{6a}$ and $R_{6c}$ are as defined and $R_{5b}$ and $R_{6b}$ together are a C—C bond can be obtained when a compound of the formula V

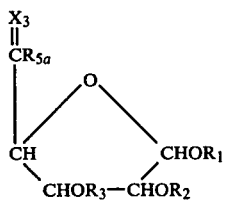

in which $R_1$, $R_2$, $R_3$ and $R_{5a}$ are as defined above, is reacted with a compound $X_4$=$CR_{6a}R_{6c}$, in which $R_{6a}$ and $R_{6c}$ are as defined above, the radical $X_3$ is oxo and $X_4$ is a radical which is detachable with the formation of a C—C double bond, $X_3+X_4$ being eliminated.

A radical $X_4$ which is detachable with the formation of a C—C double bond, $X_3+X_4$ being eliminated, is, for example, a trisubstituted phosphorus atom which is bonded by two bonds to the C atom carrying $X_4$. Suitable substituents on the phosphorus atom are, for example, lower alkoxy radicals, such as ethoxy radicals, lower alkyl radicals, such as butyl radicals, and especially aryl radicals, such as polynuclear or especially mononuclear aryl, such as naphthyl, for example 1- or 2-naphthyl, or especially phenyl, and aryl radicals can also be substituted. The nature of the aryl substituents is not of decisive importance in the process according to the invention since the phosphorus radical $X_4$ linked by a double bond is detached during the preparation of the novel hexafuranosides and is no longer contained in the novel hexafuranosides. Suitable substituents of the aryl radicals are, for example, those mentioned for aryl $R_{6c}$. In particular, $X_4$ is the radical $(C_6H_5)_3P$=. The reaction of a compound of the formula V with a compound $X_4$=$CR_{6a}R_{6c}$ is carried out in a conventional manner, especially in an inert organic solvent, for example in an ether, such as a di-lower alkyl ether, especially diethyl ether, or in a cyclic ether, such as tetrahydrofurane or dioxane, a hydrocarbon, such as an alkane, for example n-hexane, or an aromatic compound, such as benzene or an alkylbenzene, such as toluene. Suitably, the reaction is carried out in an inert gas atmosphere, such as nitrogen or argon, and if appropriate at elevated temperature, especially at about 40°–80°. Advantageously, the triarylphosphine oxide formed, for example the triphenylphosphine oxide formed, is filtered off.

Furthermore, the novel hexafuranosides of the formula I in which $R_1$, $R_2$, $R_3$, $R_{5a}$, $R_{6a}$ and $R_{6c}$ are as defined, $R_{5b}$ is hydroxyl and $R_{6b}$ is hydrogen can be obtained when a compound of the formula VI

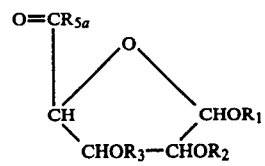

in which $R_1$, $R_2$, $R_3$ and $R_{5a}$ are as defined above, is reacted with a compound $X_5$—$CHR_{6a}R_{6c}$, in which $R_{6a}$ and $R_{6c}$ are as defined above and $X_5$ is a metal atom of group IA of the periodic system or is —Mg-Hal.

As a metal atom of group IA of the periodic system, $X_5$ is, for example, lithium or sodium. The group —Mg-Hal contains, as the radical Hal, a halogen atom, such as chlorine, bromine or iodine. The reaction is carried out in a conventional manner, preferably in an inert organic solvent, such as in an ether, for example in a di-lower alkyl ether, such as diethyl ether or dibutyl ether, or in a cyclic ether, such as tetrahydrofurane or dioxane. Advantageously, the reaction is carried out in an inert gas atmosphere, such as nitrogen or argon, and if appropriate at elevated temperature, such as at about 30°–70° C., preferably at the boiling point of the solvent used.

Furthermore, the novel hexafuranosides of the formula I in which $R_1$, $R_2$, $R_3$, $R_{5a}$, $R_{6a}$ and $R_{6c}$ are as defined, $R_{5b}$ is hydrogen, hydroxyl or lower alkoxy and $R_{6b}$ is hydroxyl can be obtained when a compound of the formula VII

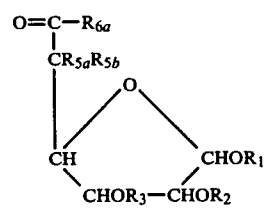

in which $R_1$, $R_2$, $R_3$, $R_{5a}$, $R_{5b}$ and $R_{6a}$ are as defined above, is reacted with a compound $X_5$—$R_{6c}$, in which $R_{6c}$ is as defined above and $X_5$ is a metal atom of group IA of the periodic system or —Mg-Hal.

As a metal atom of group IA of the periodic system, $X_5$ is, for example, lithium or sodium. The group —Mg-Hal contains, as the radical Hal, a halogen atom, such as chlorine, bromine or iodine. The reaction is carried out in a conventional manner, preferably in an inert organic solvent, such as in an ether, for example in a di-lower alkyl ether, such as diethyl ether or dibutyl ether, or in a cyclic ether, such as tetrahydrofurane or dioxane. Advantageously, the reaction is carried out in an inert gas atmosphere, such as nitrogen or argon, and if appropriate at elevated temperature, such as at about 30°–70° C.

Within the scope of the end products, it is possible to modify, introduce or detach substituents in resulting compounds, in a manner known per se, or to convert resulting compounds into other end products in a manner known per se.

Thus, in resulting compounds in which $R_1$ and $R_2$ together are an alkylidene or cycloalkylidene radical, this can be detached by reaction with an alcohol $HOR_1$.

This reaction is carried out in a manner known per se, preferably in the presence of an acid. Suitable acids are, for example, inorganic acids, such as mineral acids, for example hydrogen halide acids, such as hydrochloric acid or hydrobromic acid, and also sulphuric acid or phosphoric acid, or organic acids, such as carboxylic acids, for example lower alkanecarboxylic acids, such as acetic acid or formic acid, or lower alkanedicarboxylic acids, such as oxalic acid, or organic sulphonic acids, such as benzenesulphonic acid or p-toluenesulphonic acid, or a mixture of acids, such as a mixture of hydrogen halide acids and sulphonic acids, for example a mixture of hydrochloric acid and p-toluenesulphonic acid, or a mixture of hydrogen halide acids and lower alkanecarboxylic acids, for example a mixture of hydrochloric acid and acetic acid, preferably in the form of glacial acetic acid. Suitable acids are, in particular, also acid forms of ion exchange resins.

The said reaction with an alcohol $HOR_1$ is preferably carried out in the presence of a solvent and the alcohol $HOR_1$ can serve as the solvent. An acid used, for example a lower alkanecarboxylic acid, such as acetic acid, can likewise serve as the solvent. A hydrogen halide acid, especially hydrochloric acid, in an alcohol, such as $HOR_1$, is particularly suitable. The reaction is preferably carried out at about 0° to 25° C. or with warming at about 25° C. to 150° C., if appropriate in a closed vessel under pressure and/or in an inert gas atmosphere, such as under nitrogen or argon.

Furthermore, in resulting compounds in which $R_2$ is hydrogen, hydrogen $R_2$ can be replaced by acyl $R_2$. The replacement is effected using either a 2-OH compound of the formula I or a corresponding compound in which the 2-OH group has been converted into a reactive esterified hydroxyl group, such as one of those mentioned above, and especially into a halogen atom, such as bromine or iodine, as the starting material. In a 2-OH compound of the formula I, an acyl radical $R_2$ can, for example, be introduced by acylating methods known per se, for example by reacting a 2-OH compound of the formula I with an acid corresponding to the acyl radical or preferably with a corresponding reactive derivative thereof.

An acid derivative which is preferably used, especially a derivative of a carboxylic acid, is, for example, a halide, such as the chloride, or an anhydride, including a mixed anhydride, such as the anhydride with a carbonic acid lower alkyl half-ester (which can be obtained, for example, by reacting a suitable salt, such as an ammonium salt, of the acid with a lower alkyl halogenoformate, for example ethyl chloroformate) or with a suitable substituted or unsubstituted lower alkanecarboxylic acid, for example trichloroacetic acid or pivalic acid, and also an activated ester of such an acid, for example an ester with a N-hydroxyamino or N-hydroxyimino compound, such as N-hydroxy-succinimide, or with a lower alkanol containing electron-attracting groups, for example nitro, acyl, such as lower alkanoyl, for example acetyl, or aroyl, for example benzoyl, groups or free or functionally modified carboxyl groups, such as carbo-lower alkoxy groups, for example carbomethoxy or carboethoxy groups, carbamoyl groups, for example N,N-dimethyl or N,N-diethyl-carbamoyl groups or cyano groups, especially a methanol or phenol, for example cyanomethanol or 4-nitrophenol.

If necessary the reaction is carried out in the presence of a suitable condensing agent and/or catalyst. An acid can be used, for example, in the presence of a dehydrating condensing agent, such as a carbodiimide, for example dicyclohexylcarbodiimide, if appropriate together with a catalyst, such as a copper salt, for example copper-I chloride or copper-II chloride, or a $\beta$-alkynylamine or lower alkoxy-acetylene compound, an acid halide can be used, for example, in the presence of a basic, acid-binding condensing agent, such as pyridine or a trilower alkylamine, for example triethylamine, and an anhydride can be used, for example, in the presence of a suitable carbodiimide and if appropriate of a catalyst, such as zinc chloride.

If a compound of the formula I is used in which the 2-hydroxy group is in the form of a reactive esterified hydroxyl group, such as one of those mentioned above, an acyl radical $R_2$ can advantageously be introduced by reaction with a salt of an acid corresponding to the acyl radical. Suitable salts are, for example, alkali metal salts, such as sodium salts or potassium salts, or silver salts.

In resulting compounds containing a C—C double bond, this can be hydrogenated, especially with hydrogen in the presence of a hydrogenation catalyst, such as a heavy metal, for example platinum, palladium or nickel, such as hydrogen in the presence of palladium on active charcoal. Hydrogenolytically splittable groups can be detached at the same time.

In a resulting compound containing a hydrogenolytically splittable group, in particular a hydroxyl group etherified by a substituted or unsubstituted benzyl radical, or a benzylidenedioxy group which is unsubstituted or substituted as indicated above, such a group can be converted into a hydroxyl group by methods known per se, for example by treatment with nascent or catalytically activated hydrogen, such as zinc in an acid, such as hydrochloric acid, or such as hydrogen in the presence of a noble metal catalyst, such as one of those mentioned above, for example palladium.

In a resulting compound containing an acyl radical $R_2$, an acyloxy group can be converted into a hydroxyl group, for example by hydrolysis or by alcoholysis, preferably in the presence of a mild basic agent, such as an alkali metal bicarbonate.

In a resulting compound containing an acyl radical $R_2$, the latter can be converted into a lower alkyl radical in a conventional manner. This conversion to a lowr alkyl radical is preferably carried out by treating the starting material with a lower alkanol which is free or reactively esterified, for example as indicated above. The reaction of acyloxy groups in the starting material is preferably carried out in the presence of an acid, especially of a mineral acid, such as a hydrogen halide acid, for example hydrochloric acid, or, especially in the case of the reaction with a reactive esterified lower alkanol, in the presence of a suitable acid-binding agent, for example a silver, lead or mercury salt or a corresponding oxide, or of a tertiary base, such as a tri-lower alkylamine, for example triethylamine, and metal derivatives of the lower alkanol, such as the corresponding alkali metal compounds, for example sodium compounds, or alkaline earth metal compounds, for example magnesium compounds or silver compounds, can also be used. An acid ion exchange resin can also be used instead of an acid. This reaction is preferably carried out in the presence of a solvent and a lower alkanol can itself serve as the solvent.

In resulting compounds containing a free hydroxyl group, the latter can be etherified in a manner known per se, for example as indicated for the reaction of compounds of the formula IV. Thus, in resulting compounds in which $R_2$ is hydrogen, a lower alkyl radical $R_2$ can be introduced. Thus, in resulting compounds in which $R_3$ is hydrogen, a lower alkyl radical, lower alkenyl radical or aryl-lower alkyl radical $R_3$ can be introduced. Thus, in resulting compounds in which $R_{5b}$ is hydroxyl, a lower alkoxy radical $R_{5b}$ can be introduced. Thus, in resulting compounds in which $R_{6b}$ is hydroxyl, a lower alkoxy radical $R_{6b}$ can be introduced.

In resulting compounds in which $R_{5b}$ and $R_{6b}$ together are a C—C bond, the C—C bond $R_{5b}R_{6b}$ can be converted to an epoxy group $R_{5b}R_{6b}$. This can be effected in a manner known per se, for example generally with organic per-acids, such as lower alkanepercarboxylic acids, for example peracetic acid, or especially with aromatic percarboxylic acids, such as perbenzoic acid, a m-halogeno-perbenzoic acid, such as especially m-chloroperbenzoic acid, or monoperphthalic acid. The starting materials preferably do not contain a further aliphatic C—C double bond in addition to the C—C double bond comprising $R_{5b}R_{6b}$.

In resulting compounds in which $R_{5b}$ and $R_{6b}$ together are epoxy, epoxy $R_{5b}R_{6b}$ can be converted in a manner known per se to lower alkoxy $R_{5b}$ and hydroxyl $R_{6b}$ and/or to hydroxyl $R_{5b}$ and lower alkoxy $R_{6b}$, especially by reaction with a lower alkanol, preferably in the presence of a base, such as an alkali metal hydroxide, for example sodium hydroxide or potassium hydroxide, or especially by reaction with a lower alkanolate, for example an alkali metal lower alkanolate, such as a sodium lower alkanolate or potassium lower alkanolate. Preferably, an excess of the lower alkanol is used as the solvent.

In resulting compounds in which $R_{5b}$ and $R_{6b}$ together are epoxy, epoxy $R_{5b}R_{6b}$ can be converted in a manner known per se to hydroxyl $R_{5b}$ and hydroxyl $R_{6b}$, for example by reaction with water, preferably in the presence of a base, such as a strong inorganic base, for example an alkali metal hydroxide, such as sodium hydroxide or potassium hydroxide. In order to increase the solubility of the resulting compounds, a water-miscible organic solvent, especially an alcohol, such as a lower alkanol, for example methanol or ethanol, can be added to the water.

In resulting compounds in which $R_{5b}$ and $R_{6b}$ together are a C-C bond, the C-C bond $R_{5b}R_{6b}$ can be converted in a manner known per se to lower alkylidene $R_{5b}R_{6b}$, for example by reaction with a lower alkane, which can be substituted in the same way as lower alkylidene $R_{5b}R_{6b}$ and which carries on one C atom a radical bonded by a double bond or two radicals bonded by single bonds, which radicals are detachable leaving behind an electron sextet, i.e. are detachable leaving behind a carbene. A radical which is bonded by a double bond and is detachable leaving behind a carbene is, for example, the diazo group or the carbonyl group. The reaction with a diazo-lower alkane is carried out, for example, by means of a solution of a diazo-lower alkane, such as a solution in an ether, for example a di-lower alkyl ether, such as diethyl ether. The diazo-lower alkane is advantageously converted to the desired carbene photochemically or by the action of heat. Compounds containing a carbonyl group as a radical bonded by a double bond are ketenes, especially ketene itself. The conversion to the desired carbene is preferably effected photochemically. Two radicals which are bonded by single bonds and are detachable leaving behind a carbene are, for example, halogen atoms, such as chlorine, bromine or iodine. The reaction with a geminal dihalogeno-lower alkane is carried out, for example, in the presence of strong bases, such as alkali metal hydroxides, for example sodium hydroxide or potassium hydroide, or alcoholates, for example alkali metal lower alkanolates, such as potassium tertiary butylate. Advantageously a solvent is used, such as an alcohol, for example a lower alkanol, and if desired the alcohol corresponding to the alcoholate. Advantageously, a geminal dihalogeno-lower alkane is unsubstituted on the C atom carrying the halogen atoms, i.e. the geminal dihalogeno-lower alkane is advantageously, for example, methylene chloride or methylene bromide. A geminal dihalogeno-lower alkane can, however, particularly advantageously be substituted by a halogen atom on the C atom carrying the halogen atoms, i.e. the geminal halogeno-lower alkane is advantageously, for example trichloromethane or tribromomethane. Geminal diiodo-lower alkanes, especially methylene iodide, can advantageously also be converted into carbenes in the presence of zinc/copper under gentle conditions, for example at only moderately elevated temperature in an inert solvent, such as an ether, for example a di-lower alkyl ether, such as diethyl ether. The carbene prepared from methylene iodide in this way is methylene, so that in the end product $R_{5b}$ and $R_{6b}$ together are methylene. A suitable trihalogenomethane is, for example, also a (phenylmercury)-trihalogenomethane, such as (phenylmercury)-trichloromethane, which can be treated as above.

In resulting compounds in which $R_{5b}$ and $R_{6b}$ together are epoxy, epoxy $R_{5b}R_{6b}$ can be converted into a C—C bond formed by $R_{5b}$ and $R_{6b}$ together. This can be effected in a manner known per se, for example by reacting the resulting epoxy compound with a phosphine, such as triphenylphosphine, or the reagent obtained from lithium, chlorodiphenylphosphine and methyl iodide or with hydrogen iodide and subsequently with a reducing agent, such as tin-II chloride.

In resulting compounds in which one of the radicals $R_{5b}$ and $R_{6b}$ is hydroxyl or lower alkoxy and the other is hydrogen, these radicals $R_{5b}$ and $R_{6b}$ can be converted into a C—C bond formed by $R_{5b}$ and $R_{6b}$ together. Thus, water or a lower alkanol can be eliminated from such resulting compounds and in this way a C—C double bond can be introduced. The elimination of water or of a lower alkanol is effected in a manner known per se, especially by the action of heat, i.e. by warming to about 80°–180° C., especially to 80°–150° C. Advantageously, the reaction is carried out in a high-boiling inert solvent, such as an ether, for example an ethylene glycol di-lower alkyl ether, such as ethylene glycol dimethyl ether, or a diethylene glycol di-lower alkyl ether, such as diethylene glycol dimethyl ether. If desired, catalysts such as strong acids, such as mineral acids, especially sulphuric acid or phosphoric acid, or strong bases, such as alkali metal hydroxides, for example sodium hydroxide or potassium hydroxide, can be added.

In resulting compounds in which $R_{5b}$ and $R_{6b}$ together are an α-halogeno-lower alkylidene or dihalogenomethylidene, halogen in such radicals $R_{5b}R_{6b}$ can be replaced by hydrogen. The replacement is effected in a manner known per se, especially by reduction, such as by reduction with metals, such as sodium or potassium, preferably with lithium in a solvent, such as an alcohol, for example a lower alkanol, such as t-butanol or ethanol, or with metal alloys, such as amalgams, for example alkali metal amalgams, such as sodium amalgam, or metal hydrides, such as lithium aluminium hydride, or sodium dihydro-bis-(2-methoxyethoxy)-aluminate, preferably in an inert solvent, such as a hydrocarbon, especially toluene or benzene. When the reduction is carried out carefully, and especially when metals, metal alloys or metal hydrides are used, it is possible to replace only one halogen atom in dihalogenomethylidene by hydrogen.

In resulting compounds in which $R_{5b}$ and $R_{6b}$ together are an epoxy bond, this can be converted in a manner known per se into hydroxyl $R_{5b}$ and amino $R_{6b}$ and/or into hydroxyl $R_{6b}$ and amino $R_{5b}$, especially by reaction with a primary or secondary amine in the presence of a solvent, such as an alcohol, for example ethanol.

In resulting compounds in which $R_{5b}$ and $R_{6b}$ together are a C—C bond, a cis- or trans-C—C double bond between $C_5$ and $C_6$ can be isomerised. Thus, a cis-C—C double bond can be isomerised to a trans-C—C double bond, or a trans-C—C double bond can be isomerised to a cis-C—C double bond. The form of lower energy preferentially results and in general a trans-C—C double bond preferentially forms from a cis-C—C double bond, the cis and trans designation in each case being based on the radical $R_{6c}$ and the sugar radical bonded via $C_4$. The isomerisation is effected in a manner known per se, especially by agents which form free radicals, such as by the action of UV light or by treatment with compounds which form free radicals, such as diazo compounds, for example bis-azoisobutyrodinitrile. If the isomerisation does not proceed to completion, the mixture of the cis isomer and trans isomer can be separated by methods known per se, for example as described below, or by forming a complex, such as by forming a heavy metal complex, for example with silver salts, such as silver nitrate, and in general it is preferentially the cis isomer which enters into complex formation more readily and can be separated off. The isomer which preferentially forms a complex is separated off and liberated from the complex, for example by warming; the isomer which forms a complex less readily remains behind.

In resulting compounds, a lower alken-2-yl group $R_3$ can be converted to hydrogen. Lower alken-2-yl is in particular allyl. The conversion to hydrogen is effected in a manner known per se, especially by shifting the double bond in lower alken-2-yl to a 1-double bond, i.e. to give lower alken-1-yl, preferably by treatment with strong bases, such as an alkali metal alcoholate, for example an alkali metal lower alkanolate, such as potassium tertiary butylate, especially in an inert solvent, such as a di-lower alkyl-formamide, for example dimethylformamide, or preferably in a di-lower alkyl-sulphoxide, for example dimethylsulphoxide, and subsequently removing the lower alken-1-yl formed, by oxidative hydrolysis, especially by treatment with an alkali metal permanganate, for example potassium permanganate, in a preferably basic medium, such as in potassium hydroxide solution, in particular potassium hydroxide in a lower alkanol, such as ethanol.

In the above reactions, functional groups can, if desired, temporarily be protected and set free again after carrying out the reaction. Thus, hydroxyl groups can be protected in particular as indicated above by benzyl radicals or lower alken-2-yl radicals and subsequently set free again, as indicated above.

Compounds which have a radical containing salt-forming groups, for example free carboxyl groups, can be obtained in the free form or in the form of salts, depending on the reaction conditions, and these forms can be converted into one another in a manner known per se. Salts of compounds having a free carboxyl group are, for example, metal salts, especially alkali metal salts, for example sodium salts or potassium salts, and also alkaline earth metal salts, for example magnesium salts or calcium salts, or ammonium salts, for example those with ammonia, or salts with organic bases, such as tri-lower alkylamines, for example trimethylamine or triethylamine, and especially the pharmaceutically acceptable non-toxic salts of the above type. They are obtained, for example, by treating the free compounds with metal hydroxides or metal carbonates or with ammonia or amines, and also with suitable ion exchange resins.

Compounds containing basic groups can be in the form of acid addition salts, especially pharmaceutically acceptable non-toxic salts, for example with inorganic acids, such as hydrochloric acid, hydrobromic acid, sulphuric acid or phosphoric acid, or with organic acids, such as aliphatic, cycloaliphatic, cycloaliphatic-aliphatic, aromatic, araliphatic, heterocyclic or heterocyclic-aliphatic carboxylic or sulphonic acids, for example acetic acid, propionic acid, succinic acid, glycolic acid, lactic acid, malic acid, tartaric acid, citric acid, ascorbic acid, maleic acid, phenylacetic acid, benzoic acid, 4-aminobenzoic acid, anthranilic acid, 4-hydroxybenzoic acid, salicylic acid, aminosalicyclic acid, embonic acid or nicotinic acid and also methanesulphonic acid, ethanesulphonic acid, 2-hydroxyethanesulphonic acid, ethylenesulphonic acid, benzenesulphonic acid, p-toluenesulphonic acid, naphthalenesulphonic acid, sulphanilic acid or cyclohexylsulphamic acid. Salts of this type can be obtained, for example, by treating free compounds which contain basic groups with the acids or with suitable anion exchange resins.

Because of the close relationship between the novel compounds in the free form and in the form of their salts, what is stated in this specification in respect of the free compounds or the salts thereof also applies by analogy to the corresponding salts and free compounds.

The novel compounds can also be in the form of mixtures of isomers, such as racemates or mixtures of diastereomers, or in the form of the pure isomers, such as optically active components. The separation of resulting mixtures of isomers into the pure isomers can be effected by the known methods. Racemates can be resolved into the optically active antipodes, for example, on the basis of physico-chemical differences, for example differences in the solubility, of their diastereomeric salts, or by fractional crystallisation from an optically active solvent, or by chromatography, especially thin layer chromatography, on an optically active carrier material. Advantageously, the pharmacologically more active or less toxic pure isomer and especially the more active or less toxic active antipode is isolated.

The processes described above are carried out by methods known per se, in the absence or preferably in the presence of diluents or solvents, if necessary with cooling or warming, under elevated pressure and/or in an inert gas atmosphere, such as a nitrogen atmosphere.

Taking into account all of the substituents present in the molecule, particularly gentle reaction conditions, such as short reaction times, the use of mild acid or basic agents in low concentration, stoichiometric ratios and the choice of suitable catalysts, solvents, temperature and/or pressure conditions are to be employed if necessary, especially in the presence of readily hydrolysable O-acyl radicals.

The invention also relates to those embodiments of the process in which a compound obtainable as an intermediate at any stage of the process is used as the starting material and the missing process steps are carried out, or the process is discontinued at any stage, or a starting material is formed under the reaction conditions or is used in the form of a reactive derivative, for example a salt. The starting materials used are preferably those which according to the process result in the compounds described above as being particularly valuable.

The starting materials are known or can be prepared by methods known per se.

The invention also relates to pharmaceutical compositions which contain a hexafuranoside of the formula I.

Preferred pharmaceutical compositions are those which contain a hexafuranoside of the particularly preferred ranges of compounds or individual compounds.

The pharmaceutical compositions according to the invention advantageously contain an effective amount of the active ingredient together, or mixed, with inorganic or organic, solid or liquid, pharmaceutically acceptable carriers which are suitable for enteral or parenteral administration or topical application. Such carriers are those substances which do not react with the anhydrofuranose derivatives, for example water, gelatin, lactose, starch, stearyl alcohol, magnesium stearate, talc, vegetable oils, benzyl alcohols, gum, propylene glycols, white petroleum jelly or other known medicinal carriers. The pharmaceutical compositions can be, for example, in the form of tablets, sugar-coated tablets, capsules, suppositories, creams or ointments or in liquid form as solutions (for example as an elixir or syrup), suspensions or emulsions. The pharmaceutical compositions can be sterilised and/or contain adjuncts, for example preservatives, stabilisers, wetting agents and/or emulsifiers, solubilising agents, salts for regulating the osmotic pressure and/or buffers. The pharmaceutical compositions of this specification, which, if desired, can contain further pharmacologically valuable substances, are prepared in a manner known per se, for example by conventional mixing, granulating or sugar-coating methods, and contain from about 0.1% to about 75%, especially from about 1% to about 50%, of the active ingredient.

The invention also relates to the treatment of warm-blooded animals to achieve anti-inflammatory effects by administering a pharmaceutical composition according to the invention. Advantageously, the daily dose for a warm-blooded animal weighing about 70 kg is about 200–1200 mg per day and preferably about 300–800 mg per day.

Particularly suitable pharmaceutical compositions are, furthermore, those of the abovementioned type which contain an analgesic as a further active ingredient. Suitable analgesics are especially non-narcotic analgesics, such as so-called weak analgesics, for example salicylic acid and derivatives thereof, for example acetylsalicylic acid, aniline derivatives, such as phenacetin, lactophenin, p-acetaminophenol and $\beta$-hydroxy-butyric acid p-phenetidide, pyrazolone derivatives, such as antipyrine, isopropylphenazone, Pyramidon, Novalgin, sodium 1-phenyl-2,3-dimethyl-5-pyrazolone-4-isobutylaminomethanesulphonate, isopyrin, Nicopyron, Ampylo, Tarugan and Piperylon, 3,5-dioxopyrazolidines, such as phenylbutazone, oxyphenebutazone, sulphinepyrazone, ketazone and phenyopyrazone, quinoline derivatives, such as cinchophen, Novatophan, Tolysin, chloroquines and Glafenin, anthranilic acid derivatives such as mefenamic acid, flufenamic acid, meclofenamic acid and niflumic acid and also Ibufenac, Myalex, Benzydamin and Naftypramid.

The following examples serve to illustrate the invention; temperatures are given in degrees Centigrade.

EXAMPLE 1

100 ml of the acid form of an ion exchange resin (Dowex 50 WH+50-mesh) which is saturated with absolute ethanol are added to 30 g (85 mmols) of 3-O-benzyl-5,6-dideoxy-1,2-O-isopropylidene-6-phenyl-$\alpha$-D-xylo-hex-5-eno-furanose in 650 ml of absolute ethanol. This mixture is stirred slowly with the exclusion of moisture and under reflux at a bath temperature of 75° for 55 hours. The reaction is monitored by thin layer chromatography on silica gel plates using hexane/ethyl acetate, 2:1, as the solvent, to determine whether it has ended. The reaction mixture is filtered and the filter residue of ion exchange resin is washed with 200 ml of absolute ethanol. The filtrate is evaporated to dryness at a bath temperature of 40° and under 20 mm Hg in a rotary evaporator. The residue, which is a syrup, is purified through a column (diameter 25 mm, height 550 mm) of 120 g of dry silica gel using hexane/ethyl acetate, 4:1 as the solvent. As soon as the solvent has reached the end of the column, UV light (254 nm) is used to determine precisely where in the range of Rf values 0.25 and 0.35 the enriched zones which contain the $\alpha$-anomer and $\beta$-anomer are located in the column. These zones are cut out of the column and extracted with ethanol. After evaporating the combined ethanolic solution, the mixture of the anomers of ethyl 3-O-benzyl-5,6-dideoxy-6-phenyl-D-xylo-hex-5-enofuranoside remains as a syrup.

In UV light of 254 nm, the thin layer chromatogram on a silica gel plate, using hexane/ethyl acetate, 2:1, as the solvent, shows 2 spots with Rf values of 0.31 and 0.41 which belong to the $\alpha$-anomer and $\beta$-anomer.

6.8 g (20 mmols) of the mixture of anomers are introduced into a dry column of 120 g of silica gel, having a diameter of 25 mm and a length of 550 mm, and separated using hexane/ethyl acetate, 4:1, as the solvent.

Two zones are characterised in UV light of 254 nm and these are cut out of the column and extracted with ether. After evaporating the ether extracts, a syrup with an $[\alpha]_D^{23} = -56.23°$ (c=2.1 in chloroform) and a spot indicating a single compound in the thin layer chromatogram (Rf=0.35, solvent=hexane/ethyl acetate, 3:1) and a solid fraction having a melting point of 46°–51°, an $[\alpha]_D^{24} = -42.66°$ (c=1.8 in chloroform) and a spot indicating a single compound in the thin layer chromatogram (Rf=0.2, solvent=hexane/ethyl acetate, 3:1) are obtained. Each fraction consists to the extent of more than 90% of the cis isomer of the particular anomer.

EXAMPLE 2

A solution of 19.0 g of 1,2-O-isopropylidene-3-O-n-propyl-5,6-dideoxy-6-(4-chlorophenyl)-D-xylo-cis-hex-5-enofuranose in 300 ml of a 1 N solution of hydrogen chloride in ethanol is allowed to stand for 16 hours at about 25° and the reaction mixture is then freed from the bulk of the ethanolic hydrogen chloride under a waterpump vacuum and at 30°. After cooling the residue to 0°–5°, this is extracted with diethyl ether. The organic extracts are washed with ice-cold saturated aqueous sodium bicarbonate solution and with ice-water until neutral, dried over sodium sulphate and filtered and the filtrate is evaporated. The residue is purified by column chromatography on silica gel, by elution with methylene chloride/ethyl acetate (85:15). Ethyl 6-(4-chlorophenyl)-5,6-dideoxy-3-O-n-propyl-D-xylo-cis-hex-5-enofuranoside, which thus results, is obtained in the form of a yellowish oil of Rf=0.40 and 0.55 and is a mixture of anomers (thin layer chromatography on silica gel in the system methylene chloride/ethyl acetate (85:15)) and has an $[\alpha]_D^{20} = +51° \pm 1°$ (chloroform, c=1.022).

The starting material can be prepared as follows:

A solution of 32.2 g of 1,2-O-isopropylidene-3-O-n-propyl-5-aldehydo-α-D-xylo-pentafuranose in 140 ml of dry dimethylsulphoxide is added dropwise, at 30°, with the exclusion of moisture and in a nitrogen atmosphere, in the course of 2 hours to a stirred suspension of 6.6 g of a 55–60% strength dispersion of sodium hydride, which has previously been washed with petroleum ether, and 63.4 g of p-chlorobenzyl-triphenylphosphonium chloride in 200 ml of dimethylsulphoxide. After stirring for a further one hour, the reaction mixture is filtered and the filtrate is poured into 300 ml of ice-water and extracted with ether. The ether solution is washed with water, dried over sodium sulphate and filtered through 200 g of aluminium oxide to give a neutral filtrate. After distilling off the ether and degassing the residue under a high vacuum, 1,2-O-isopropylidene-3-O-n-propyl-5,6-dideoxy-6-p-chlorophenyl-α-D-xylo-cis-hex-5-enofuranose is obtained and this is further processed without further purification.

EXAMPLE 3

41 g of 1,2-O-isopropylidene-3-O-n-propyl-5,6-dideoxy-6-phenyl-α-D-xylo-cis-hex-5-enofuranose and 540 ml of a 1 N solution of hydrogen chloride in ethanol are treated as described in Example 2. The resulting ethyl 5,6-dideoxy-6-phenyl-3-O-n-propyl-D-xylo-cis-hex-5-enofuranoside is obtained in the form of a yellowish oil of Rf=0.36 and 0.58 and is a mixture of anomers (thin layer chromatography on silica gel) in the system methylene chloride/ethyl acetate (85:15) and has an $[\alpha]_D^{20} = +29° \pm 1°$ (chloroform, c=1.169).

The starting material can be prepared as follows:
72 g of 1,2-O-isopropylidene-3-O-n-propyl-5-aldehydo-α-D-xylopentofuranose in 360 ml of dimethylsulphoxide, 14.8 g of a 55–60% strength dispersion of sodium hydride, which has been washed with petroleum ether, and 131 g of benzyl-triphenylphosphonium chloride in 400 ml of dimethylsulphoxide are treated as in Example 2. The resulting 1,2-O-isopropylidene-3-O-n-propyl-5,6-dideoxy-6-phenyl-α-D-xylo-cis-5-hexenofuranose is further processed without further purification.

EXAMPLE 4

A solution of 23.0 g of 1,2-O-isopropylidene-3-O-n-propyl-5,6-dideoxy-6-phenyl-α-D-xylo-cis-hex-5-enofuranose in 300 ml of a 1 N solution of hydrogen chloride in n-butanol is left to stand for 16 hours at about 25°. The reaction mixture is then freed from the bulk of the n-butanolic hydrochloric acid. The residue is dissolved in ether and the ether solution is washed with a saturated solution of sodium bicarbonate and with water until neutral. After drying the ether phase over sodium sulphate and filtering, the filtrate is evaporated. The residue, which is degassed under a high vacuum, is pure n-butyl 5,6-dideoxy-6-phenyl-3-O-n-propyl-D-xylo-cis-hex-5-enofuranoside in the form of a yellowish oil of Rf=0.55 and 0.68 and is a mixture of anomers (thin layer chromatography on silica gel) in the system methylene chloride/ethyl acetate (85:15) and has an $[\alpha]_D^{20} = +36° \pm 1°$ (chloroform, c=1.054).

EXAMPLE 5

A solution of 20.5 g of 1,2-O-isopropylidene-3-O-n-propyl-5,6-dideoxy-6-p-chlorophenyl-α-D-xylo-cis-hex-5-enofuranose in 300 ml of a 1 N solution of hydrogen chloride in n-butanol is treated as described in Example 4. The residue, which is degassed under a high vacuum at 60°, is n-butyl 6-(4-chlorophenyl)-5,6-dideoxy-3-O-n-propyl-D-xylo-cis-hex-5-enofuranoside, a yellowish oil of Rf=0.53 and 0.64, and is a mixture of anomers (thin layer chromatography on silica gel) in the system methylene chloride/ethyl acetate (85:15) and has a $[\alpha]_D^{20} = +48° \pm 1°$ (chloroform, c=1.188).

EXAMPLE 6

A solution of 20 g of 1,2-O-isopropylidene-3-O-benzyl-5,6-dideoxy-6-phenyl-α-D-xylo-cis-hex-5-enofuranose in 300 ml of a 1 N solution of hydrogen chloride in n-butanol is treated as described in Example 4. The resulting residue is purified by column chromatography on silica gel, by elution with methylene chloride/ethyl acetate (85:15). The resulting n-butyl 3-O-benzyl-5,6-dideoxy-6-phenyl-D-xylo-cis-hex-5-enofuranoside is obtained in the form of a yellowish oil of Rf=0.51 and 0.64 and is a mixture of anomers (thin layer chromatography on silica gel) in the system methylene chloride/ethyl acetate (85:15) and has an $[\alpha]_D^{20} = -14° \pm 1°$ (chloroform, c=1.015).

The starting material can be prepared as follows:
47.0 g of 1,2-O-isopropylidene-3-O-benzyl-5-aldehydo-α-D-xylopentofuranose, 8.3 g of a 55–60% strength dispersion of sodium hydride, 70 g of triphenyl-benzylphosphonium chloride and 500 ml of dimethylsulphoxide are treated as described in Example 2. This gives 1,2-O-isopropylidene-3-O-benzyl-5,6-dideoxy-6-phenyl-α-D-xylo-cis-hex-5-enofuranose, which is further processed without further purification.

EXAMPLE 7

A solution of 18.0 g of 1,2-O-isopropylidene-3-O-benzyl-5,6-dideoxy-6-p-chlorophenyl-α-D-xylo-cis-hex-5-enofuranose in 300 ml of a 1 N solution of hydrogen chloride in ethanol is treated as described in Example 2. After drying over sodium sulphate and filtering, evaporating the filtrate under a water-pump vacuum and degassing the residue under a high vacuum at 60°, pure ethyl 3-O-benzyl-6-(4-chlorophenyl)-5,6-dideoxy-D-xylo-cis-hex-5-enofuranoside is obtained in the form of a yellow oil of $R_f = 0.43$ and 0.58 and is a mixture of anomers (thin layer chromatography on silica gel) in the system methylene chloride/ethyl acetate (85:15) and has an $[\alpha]_D^{20} = -28° \pm 1°$ (chloroform, c=1.073).

The starting material can be prepared as follows:

70.0 g of 1,2-O-isopropylidene-3-O-benzyl-5-aldehydo-α-D-xylopentofuranose, 11.8 g of a 55–60% strength dispersion of sodium hydride, 110 g of triphenyl-p-chlorobenzyl-phosphonium chloride and 700 ml of dimethylsulphoxide are treated as described in Example 2. This gives 1,2-O-isopropylidene-3-O-benzyl-5,6-dideoxy-6-p-chlorophenyl-α-D-xylo-cis-5-hex-enofuranose, which is further processed without further purification.

EXAMPLE 8

A solution of 18.0 g of 1,2-O-isopropylidene-3-O-benzyl-5,6-dideoxy-6-p-chlorophenyl-α-D-xylo-cis-hex-5-enofuranose in 300 ml of a 1 N solution of hydrogen chloride in n-butanol is left to stand for 16 hours at about 25° and the bulk of the hydrogen chloride and n-butanol is then distilled off under reduced pressure at 30°. The residue is extracted at 0°-5° with diethyl ether. The ether solution is washed with a saturated solution of sodium bicarbonate and with water until neutral, dried over sodium sulphate and filtered and the filtrate is evaporated. After degassing under a high vacuum at 60°, the resulting residue is pure n-butyl 3-O-benzyl-6-(4-chlorophenyl)-5,6-dideoxy-D-xylo-cis-hex-5-enofuranoside, a yellowish oil of $R_f = 0.56$ and 0.66, and is a mixture of anomers (thin layer chromatography on silica gel) in the system methylene chloride/ethyl acetate (85:15) and has an optical rotation $[\alpha]_D^{20} = -24° \pm 1°$ (chloroform, c=1.078).

EXAMPLE 9

A solution of 25.4 g of ethyl 2-O-acetylsalicyloyl-6-(4-chlorophenyl)-5,6-dideoxy-3-O-n-propyl-D-xylo-cis-hex-5-enofuranoside in 300 ml of a 1 N solution of hydrogen chloride in ethanol is allowed to stand for 16 hours at about 25° and, after working up and purifying as described in Example 2, ethyl 2-O-salicyloyl-6-(4-chlorophenyl)-5,6-dideoxy-3-O-n-propyl-D-xylo-cis-hex-5-enofuranoside is obtained in the form of a yellowish oil of $R_f = 0.72$ (thin layer chromatography on silica gel) in the system methylene chloride/ethyl acetate (85:15), and $[\alpha]_D^{20} = +29° \pm 1°$ (methylene chloride, c=1.232).

EXAMPLE 10

A solution of 12.7 g of acetylsalicyloyl chloride in 50 ml of methylene chloride is added dropwise in the course of 3 hours, at $-10°$ to $0°$ with the exclusion of moisture, to a solution of 17.4 g of ethyl 6-(4-chlorophenyl)-5,6-dideoxy-3-O-n-propyl-D-xylo-cis-hex-5-enofuranoside in 50 ml of pyridine and 25 ml of methylene chloride. 20 ml of water are then added to the reaction mixture. After stirring for 30 minutes, the bulk of the methylene chloride and pyridine is evaporated off. The resulting residue is extracted with diethyl ether. The ether solution is washed with ice-water, ice-cold 1 N hydrochloric acid and a saturated solution of sodium bicarbonate and with water. After drying over sodium sulphate and evaporating, ethyl 2-O-acetylsalicyloyl-6-(4-chlorophenyl)-5,6-dideoxy-3-O-n-propyl-D-xylo-cis-hex-5-enofuranoside is obtained and this is employed in the next stage without further purification.

EXAMPLE 11

11.8 g of 1,2-O-isopropylidene-3-O-n-propyl-5-deoxy-5-C-benzyl-α-D-xylofuranose dissolved in 300 ml of a 1 N solution of hydrogen chloride in ethanol are left to stand for 16 hours at about 20° and the solution is then freed from the bulk of the ethyl alcohol and the hydrochloric acid at 40° under reduced pressure. After cooling the residue to 0°-5°, it is neutralised with a saturated aqueous solution of sodium bicarbonate and extracted with diethyl ether. The organic extract is washed with a saturated aqueous solution of sodium bicarbonate and water, dried over sodium sulphate and filtered and the filtrate is evaporated under reduced pressure. After distilling the residue in a bulb tube under a high vacuum, pure ethyl 3-O-n-propyl-5-deoxy-5-C-benzyl-D-xylofuranoside is obtained in the form of a colourless oil, $[\alpha]_D^{20} = +26° \pm 1°$ (c=1.303 in chloroform), boiling point 140°-145° under 0.03 mm Hg.

The starting material can be obtained as follows: 1.5 g of 5% strength palladium-on-charcoal are added to a solution of 15.2 g of 1,2-O-isopropylidene-3-O-n-propyl-5,6-di-deoxy-6-phenyl-α-D-xylo-cis-hex-5-enofuranose in 150 ml of methanol and the solution is hydrogenated with 1,170 ml of hydrogen, with shaking. The reaction mixture is filtered and the filtrate is freed from methanol. After degassing the residue under a high vacuum, pure 1,2-O-isopropylidene-3-O-n-propyl-5-deoxy-5-C-benzyl-α-D-xylofuranose of $R_f = 0.45$ (thin layer chromatography on silica gel) in the system methylene chloride and an optical rotation $[\alpha]_D^{20} = -33° \pm 1°$ (c=0.227 in chloroform) is obtained.

EXAMPLE 12

A solution of 6.5 g of 1,2-O-isopropylidene-3-O-benzyl-4-C-(2-phenyl-cyclopropyl-1)-α-D-xylo-tetrofuranose in 130 ml of absolute ethanol is refluxed in the presence of 18 ml of acid ion exchange resin (Dowex 50 H+) saturated with absolute ethanol and 1 ml of a 3 Å molecular sieve for 21 hours. The reaction mixture is then filtered, the material on the filter is washed with a little ethanol and the excess ethanol is evaporated from the filtrate. The residue is eluted by column chromatography on 700 g of silica gel using hexane/ethyl acetate (2:1). The product of $R_f = 0.4$ (thin layer chromatography on silica gel) in the system hexane/ethyl acetate (2:1), and optical rotation $[\alpha]_D^{22} = +8.09°$ (c=3.4 in chloroform) is ethyl 3-O-benzyl-4-C-(cis-2-phenyl-cyclopropyl-1)-α-D-xylo-tetrofuranoside in the form of a yellowish oil.

The product of $R_f = 0.3$ (thin layer chromatography on silica gel) in the system hexane/ethyl acetate (2:1) and $[\alpha]_D^{22} = -95.14°$ (c=3.4 in chloroform) is ethyl 3-O-benzyl-4-C-(cis-2-phenyl-cyclopropyl-1)-β-D-xylo-tetrofuranoside in the form of a yellowish oil.

The starting material can be prepared as follows:

One drop of methylene iodide is added to a suspension of 60 millimols of zinc powder coated with copper (E. Le Goff, J. Org. Chem. 29, 2048 (1960)) in 15 ml of absolute ether, so that the reaction starts. Subsequently, a solution of 9.5 g (27 mmols) of 1,2-O-isopropylidene-3-O-benzyl-5,6-dideoxy-6-phenyl-α-D-xylo-cis-hex-enofuranose in 10 ml of absolute ether is added dropwise at such a rate that the reaction mixture refluxes gently. After the dropwise addition, the reaction mixture is refluxed for a further 16 hours and filtered with a filter aid and the material on the filter is washed with ether. The ether solution is washed with 1 N hydrochloric acid and a saturated solution of sodium bicarbonate and with water, dried over sodium sulphate and filtered and the filtrate is evaporated. The resulting residue is eluted by column chromatography on 700 g of silica gel using hexane/ethyl acetate (5:1). The fraction which is obtained after evaporation and has been degassed under a high vacuum and has a $R_f$ value of 0.30 (thin layer chromatography on silica gel) in the system hexane/ethyl acetate (5:1) is pure 1,2-O-isopropylidene-3-O-benzyl-4-C-(cis-2-phenyl-cyclopropyl-1)-α-D-xylo-tetrofuranose with an optical rotation $[\alpha]_D^{23} = -96.7°$ (c=1.5 in chloroform).

EXAMPLE 13

A solution of 17 g of 1,2-O-isopropylidene-3-O-benzyl-4-C-(cis-2,2-dichloro-3-phenyl-cyclopropyl-1)-α-D-xylo-tetrofuranose in 240 ml of absolute ethanol is refluxed in the presence of 55 ml of acid ion exchange resin (Dowex 50 H+) (saturated with absolute ethanol) for 48 hours. Subsequently, the reaction mixture is worked up, and the product purified, as described in Example 13. This gives ethyl 3-O-benzyl-4-C-(cis-2,2-dichloro-3-phenyl-cyclopropyl-1)-4-α-D-xylo-tetrofuranoside in the form of a yellowish oil of $R_f = 0.50$ (thin layer chromatography on silica gel) in the system hexane/ethyl acetate (2:1) and $[\alpha]_D^{20} = +27.4°$ (c=1.8 in chloroform) and ethyl 3-O-benzyl-4-C-(cis-2,2-dichloro-3-phenyl-cyclopropyl-1)-4-β-D-xylo-tetrofuranoside in the form of a yellowish oil of $R_f = 0.60$ (thin layer chromatography on silica gel) in the system hexane/ethyl acetate (2:1) and $[\alpha]_D^{20} = -30.8°$ (c=1.6 in chloroform).

The starting material can be prepared as follows:

6.8 g of potassium tertiary butylate are added to a solution, which has been cooled to −20°, of 16.8 g of 1,2-O-isopropylidene-3-O-benzyl-5,6-dideoxy-6-phenyl-α-D-xylo-cis-hex-5-enofuranose, and a mixture of 5 ml of chloroform and 5 ml of pentane is then dropwise in the course of 2 hours at −20°/−25°. The mixture is then allowed to warm to about 20°. This procedure with the chloroform and potassium tertiary butylate is repeated a further 3 times at 1 day intervals. The reaction mixture is then filtered with a filter aid and the material on the filter is washed with pentane. The residue obtained after evaporating the filtrate is eluted by column chromatography on 1.2 kg of silica gel using hexane/ethyl acetate (5:1). The product of $R_f = 0.45$ (thin layer chromatography on silica gel) in the system hexane/ethyl acetate (5:1) is pure 1,2-O-isopropylidene-3-O-benzyl-4-C-(cis-2,2-dichloro-3-phenyl-cyclopropyl-1)-α-D-xylo-tetrofuranose with a melting point of 75.4°–79.8° and an optical rotation $[\alpha]_D^{25} = -53.1°$ (c=1.3 in chloroform).

EXAMPLE 14

Under conditions the same as those described in Example 2, a solution of 47.0 g of 1,2-O-isopropylidene-3-O-benzyl-5-aldehydo-α-D-xylo-pentafuranose in 150 ml of dry dimethylsulphoxide is allowed to react with 8.3 g of a sodium hydride dispersion (55–60% strength) and 70 g of benzyl-triphenyl-phosphonium chloride and the reaction mixture is worked up. After distilling off the ether and degassing the residue under a high vacuum, 1,2-O-isopropylidene-3-O-benzyl-5,6-dideoxy-6-phenyl-α-D-xylo-cis-hex-5-enofuranose is obtained in the form of a yellowish oil of $R_f = 0.50$ (thin layer chromatography on silica gel) in the system methylene chloride and an optical rotation $[\alpha]_D^{20} = -77° \pm 1°$ (c=1.104 in chloroform), and ethyl 3-O-benzyl-5,6-dideoxy-6-phenyl-D-xylo-cis-hex-5-enofuranoside is obtained from this in accordance with Example 1.

EXAMPLE 15

Analogously to Example 2, a solution of 52.5 g of 1,2-O-isopropylidene-3-O-benzyl-5-aldehydo-α-D-xylo-pentofuranose in 240 ml of dry dimethylsulphoxide is reacted with 9.2 g of a sodium hydride dispersion (55–60% strength) and 93 g of 4-methyl-phenyl-triphenyl-phosphonium bromide and the reaction mixture is worked up. After distilling off the ether and crystallising the residue from petroleum ether, 1,2-O-isopropylidene-3-O-benzyl-5,6-dideoxy-6-(4-methyl-phenyl)-α-D-xylo-cis-hex-5-enofuranose is obtained in the form of white crystals with a melting point of 70°–71° C. and an optical rotation $[\alpha]_D^{20} = -134° \pm 1°$ (c=1.350 in chloroform).

EXAMPLE 16

In the manner described in Example 2, a solution of 64.0 g of 1,2-O-isopropylidene-3-O-benzyl-5-aldehydo-α-D-xylo-pentofuranose in 270 ml of dry dimethylsulphoxide is reacted with 10.2 g of a sodium hydride dispersion (55–60% strength) and 96.0 g of 4-methoxy-phenyl-triphenyl-phosphonium chloride and the reaction mixture is worked up. After distilling off the ether and crystallising the residue from petroleum ether, 1,2-O-isopropylidene-3-O-benzyl-5,6-dideoxy-6-(4-methoxy-phenyl)-α-D-xylo-cis-hex-5-enofuranose is obtained in the form of white crystals with a melting point of 51°–52° C. and an optical rotation $[\alpha]_D^{20} = -117° \pm 1°$ (c=1.232 in chloroform).

EXAMPLE 17

A solution of 30.4 g of 1,2-O-isopropylidene-3-O-n-propyl-5,6-dideoxy-6-phenyl-α-D-xylo-cis-hex-5-enofuranose and 22.2 g of m-chloroperbenzoic acid (85% strength) in 250 ml of methylene chloride is stirred at room temperature for 15 hours with the exclusion of moisture. The m-chlorobenzoic acid which has formed is then filtered off and the filtrate is washed with 1 N sodium hydroxide solution, water, 10% strength iron-II sulphate solution, 1 N sodium hydroxide solution and again with water. After drying the methylene chloride phase over magnesium sulphate and evaporating and crystallising the resulting residue, pure 1,2-O-isopropylidene-3-O-n-propyl-5,6-anhydro-6-C-phenyl-β-L-glycero-L-ido-hexafuranose with a melting point of 84°–85° and an optical rotation $[\alpha]_D^{20} = -120° \pm 1°$ (c=1.14 in choroform) is obtained.

EXAMPLE 18

A solution of 6.4 g of 1,2-O-isopropylidene-3-O-n-propyl-5,6-anhydro-6-C-phenyl-β-L-glycero-L-ido-hexofuranose and 7.2 g of isopropylamine in 10 ml of ethanol is refluxed for 15 hours. The reaction mixture is then evaporated and the resulting residue is dissolved in ether. The ether solution is washed with 2 N hydrochloric acid and with water. The combined hydrochloric acid and water phases are rendered alkaline with 10 N sodium hydroxide solution and extracted with ether. The ether phases are washed with a little water, dried over magnesium sulphate and evaporated. Degassing the resulting residue under a high vacuum gives pure 1,2-O-isopropylidene-3-O-n-propyl-6-deoxy-6-isopropylamino-6-C-phenyl-β-L-idofuranose in the form of a colourless oil of $R_f=0.35$ (thin layer chromatography on silica gel) in the system methylene chloride/methanol (15:1) and an optical rotation $[\alpha]_D^{20}=-27°\pm1°$ (c=1.294 in chloroform).

EXAMPLE 19

1,2-O-Isopropylidene-3-O-benzyl-5,6-anhydro-6-C-(4-methylphenyl)-β-L-glycero-L-ido-hexofuranose of melting point=72°–74° C. and an optical rotation $[\alpha]_D^{20}=-118°\pm1°$ (c=1.033 in chloroform) is obtained analogously to Example 17 from 15.0 g of 1,2-O-isopropylidene-3-O-benzyl-5,6-dideoxy-6-C-(4-methylphenyl)-α-D-xylo-cis-hex-5-enofuranose and 9.1 g of m-chloroperbenzoic acid (85% strength) in 150 ml of methylene chloride.

EXAMPLE 20

44.0 g of chlorodiphenylphosphine are added dropwise to a mixture of 6 g of finely shredded lithium metal in 200 ml of dry tetrahydrofurane, with stirring, at room temperature and in a nitrogen atmosphere. The mixture is left to stand for 12 hours and a solution of 50.0 g of 1,2-O-isopropylidene-3-O-benzyl-5,6-anhydro-6-C-phenyl-β-L-glycero-L-ido-hexofuranose in 1,360 ml of dry tetrahydrofurane is then added dropwise at room temperature. After stirring for a further 12 hours, 58 g of methyl iodide are added and the mixture is stirred for a further 1 hour. The reaction mixture is filtered and evaporated. The resulting residue is dissolved in ether and the solution is washed with water until neutral and, after drying over magnesium sulphate, is evaporated. After crystallisation from ethanol, the residue is pure 1,2-O-isopropylidene-3-O-benzyl-5,6-dideoxy-6-C-phenyl-α-D-xylo-transhex-5-enofuranose in the form of white crystals with a melting point of 96°–97° C. and an optical rotation $[\alpha]_D^{20}=-10°\pm1°$ (c=1.214 in chloroform).

EXAMPLE 21

A solution of 9.2 g of 1,2-O-isopropylidene-3-O-benzyl-4-C-(trans-2-phenyl-cyclopropyl-1)-α-D-xylo-tetrofuranose in 190 ml of absolute ethanol is stirred in the presence of 45 g of acid ion exchange resin (Amberlite JR 120) (saturated with absolute ethanol and 1 ml of a 3 Å molecular sieve) for 21 hours at room temperature. The reaction mixture is then filtered, the material on the filter is washed with a little ethanol and the excess ethanol is evaporated from the filtrate. The residue is eluted by column chromatography on 700 g of silica gel using methylene chloride/ethyl acetate (85:15). The product of $R_f=0.58$ (thin layer chromatography on silica gel) in the system methylene chloride/ethyl acetate (85:15), an optical rotation $[\alpha]_D^{20}=+111°\pm1°$ (c=0.994 in chloroform) and of a melting point of 69°–70° C. is ethyl 3-O-benzyl-4-C-(trans-2-phenyl-cyclopropyl-1)-α-D-xylo-tetrofuranoside in the form of white crystals.

The product of $R_f=0.34$ (thin layer chromatography on silica gel) in the system methylene chloride/ethyl acetate (85:15), $[\alpha]_D^{20}=+13°\pm1°$ (c=1.054 in chloroform) and a melting point of 65°–66° C. is ethyl 3-O-benzyl-4-C-(trans-2-phenylcyclopropyl-1)-β-D-xylo-tetrofuranoside in the form of white crystals.

The starting material can be prepared as follows:
One drop of methylene iodide is added to a suspension of 60 millimols of zinc powder coated with copper (E. Le Goff, J. Org. Chem. 29, 2048 (1960)) in 15 ml of absolute ether, so that the reaction starts. A solution of 9.5 g (27 mmols) of 1,2-O-isopropylidene-3-O-benzyl-5,6-dideoxy-6-phenyl-α-D-xylo-trans-hex-5-enofuranose in 10 ml of absolute ether is then added dropwise at such a rate that the reaction mixture refluxes gently. After the dropwise addition, the reaction mixture is refluxed for a further 16 hours and filtered with a filter aid and the material on the filter is washed with ether. The ether solution is washed with 1 N hydrochloric acid and a saturated solution of sodium bicarbonate and with water, dried over sodium sulphate and filtered and the filtrate is evaporated. After crystallisation from ethanol, the resulting residue is pure 1,2-O-isopropylidene-3-O-benzyl-4-C-(trans-2-phenyl-cyclopropyl-1)-α-D-xylo-tetrofuranose with a melting point of 109°–110° C., a Rf=0.25 (thin layer chromatography on silica gel) in the system methylene chloride and an optical rotation $[\alpha]_D^{20}=+38°\pm1°$ (c=1.042 in chloroform).

EXAMPLE 22

1,2-O-Isopropylidene-3-O-benzyl-5,6-anhydro-6-C-phenyl-β-L-glycero-L-iso-hexofuranose with a melting point of 96°–97° C. and an optical rotation $[\alpha]_D^{20}=-108°\pm1°$ (c=1.140 in chloroform) is obtained analogously to Example 17 from 72 g of 1,2-O-isopropylidene-3-O-benzyl-5,6-dideoxy-6-C-phenyl-α-D-xylo-cis-hex-5-enofuranose and 45.5 g m-chloroperbenzoic acid (85% strength) in 720 ml of methylene chloride.

EXAMPLE 23

A solution of 14.7 g of 1,2-O-isopropylidene-3-O-benzyl-4-C-(2,2-dichloro-3-S-phenyl-cyclopropyl-1-R)-α-D-xylo-tetrofuranose in 60 ml of dioxane is added to a stirred suspension of 3.7 g of lithium aluminium hydride in 140 ml of dioxane and the mixture is refluxed for 15 hours. After the reaction mixture has cooled, first ethyl acetate and then a little 2 N hydrochloric acid are added and the resulting mixture is filtered through Hyflo-Supercel. The residue from the evaporated filtrate is dissolved in ether and the solution is washed with water until neutral. The ether solution is evaporated and the residue is crystallised from ether/petroleum ether. The resulting white crystals are pure 1,2-O-isopropylidene-3-O-benzyl-4-C-(2-S-chloro-3-S-phenyl-cyclopropyl-1-R)-α-D-xylo-tetrofuranose with a melting point of 138°–140° C. and an optical rotation $[\alpha]_D^{20}=-112°\pm1°$ (c=1.002 in chloroform).

Pure 1,2-O-isopropylidene-3-O-benzyl-4-C-(2-R-chloro-3-S-phenyl-cyclopropyl-1-R)-α-D-xylo-tetrofuranose with a melting point of 67°–68° and an optical rotation $[\alpha]_D^{20}=-82°\pm1°$ (c=1.017 in chloroform) is obtained by purifying the mother liquor by chromatography on 250 g of silica gel using methylene chloride as the eluant, after crystallising the residue from methanol.

EXAMPLE 24

9.6 g of methanesulphonic acid are added to a solution of 7.0 g of 1,2-O-isopropylidene-3-O-n-propyl-4-C-(cis-2-phenylcyclopropyl-1)-α-D-xylo-tetrofuranose in 100 ml of absolute ethanol, with external ice-cooling and with stirring, and the mixture is then allowed to react for 16 hours with the exclusion of light and moisture. 52 ml of ice-cold 2 N sodium hydroxide solution are added to the reaction solution and the resulting mixture is freed from the bulk of the ethanol under reduced pressure. The residue is taken up in ether and the solution is washed with water until neutral, dried over magnesium sulphate and filtered and the filtrate is evaporated. The residue is degassed under a high vacuum. This gives pure ethyl 3-O-n-propyl-4-C-(cis-2-phenyl-cyclopropyl-1)-D-xylotetrofuranoside in the form of a colourless oil, with a Rf=0.34 for the α-anomer and Rf=0.19 for the β-anomer (thin layer chromatography on silica gel) in the system methylene chloride/ethyl acetate (19:1), the optical rotation of the mixture being $[\alpha]_D^{20} = -4° \pm 1°$ (c=0.669 in chloroform).

The starting material can be prepared as follows:

A solution of 40.0 g of 1,2-O-isopropylidene-3-O-n-propyl-5,6-dideoxy-6-C-phenyl-α-D-xylo-cis-hex-5-enofuranose and 8.4 g of tetrabutylammonium bromide in 440 ml of chloroform is added dropwise in the course of 20 minutes to a stirred solution, externally cooled with ice/sodium chloride, of 500 ml of 10 N sodium hydroxide solution at such a rate that the temperature does not exceed 0° C. The mixture is then allowed to react for 48 hours at 0° C., with vigorous stirring. After adding 1,000 ml of chloroform, the sodium hydroxide solution is separated off and the chloroform phase is washed with water until neutral, dried over magnesium sulphate and filtered and the filtrate is evaporated. The residue is purified by column chromatography on silica gel by elution with methylene chloride. 1,2-O-Isopropylidene-3-O-n-propyl-4-C-(cis-2,2-dichloro-3-phenylcyclopropyl-1)-α-D-xylo-tetrofuranose, which thus results and has a R$_f$=0.41 (thin layer chromatography on silica gel) in the system methylene chloride and an optical rotation $[\alpha]_D^{20} = -44° \pm 1°$ (c=0.203 in chloroform), is obtained in the form of a colourless oil.

EXAMPLE 25

41 ml of a 70% strength solution of sodium dihydro-bis-(2-methoxy-ethoxy)-aluminate in benzene are added to a solution of 17.0 g of 1,2-O-isopropylidene-3-O-benzyl-4-C-(cis-2,2-dichloro-3-biphenyl-cyclopropyl-1)-α-D-xylo-tetrofuranose in 120 ml of o-xylene and the mixture is refluxed for 6 hours. After cooling, water is added carefully, 3,000 ml of ether are added, the pH is adjusted to 1 with 2 N ice-cold hydrochloric acid and the aqueous phase is separated off. The ether solution is washed with water until neutral, dried over magnesium sulphate and filtered and the filtrate is evaporated. The resulting residue is separated into two fractions by column chromatography on silica gel. These two fractions were crystallised from ethanol. The product with a melting point of 130°-33°, a R$_f$=0.45 (thin layer chromatography on silica gel) in the system methylene chloride and an optical rotation $[\alpha]_D^{20} = -78° \pm 1°$ (c=2.017 in chloroform) is 1,2-O-isopropylidene-3-O-benzyl-4-C-(trans-2-biphenyl-cyclopropyl-1)-α-D-xylo-tetrofuranose. The product with a melting point of 204°-205°, a R$_f$=0.45 (thin layer chromatography on silica gel) in the system methylene chloride and an optical rotation $[\alpha]_D^{20} = -139° \pm 1°$ (c=1.279 in chloroform) is 1,2-O-isopropylidene-3-O-benzyl-4-C-(2-S-chloro-3-R-biphenyl-cyclopropyl-1R)-α-D-xylo-tetrafuranose. The product with a melting point of 181°-83°, a Rf=0.28 (thin layer chromatography on silica gel) in the system methylene chloride and an optical rotation $[\alpha]_D^{20} = -150° \pm 1°$ (c=1.311 in chloroform) is 1,2-O-isopropylidene-3-O-benzyl-4-C-(2-S-biphenyl-cyclopropyl-1-R)-α-D-xylo-tetrofuranose.

The starting material can be prepared as follows.

A solution of 65.3 g of 1,2-O-isopropylidene-3-O-benzyl-5-aldehydo-α-D-xylo-pentofuranose in 190 ml of dry dimethyldsulphoxide is added dropwise, at 30° with the exclusion of moisture in a nitrogen atmosphere, in the course of 1 hour to a stirred suspension of 11.8 g of a 55–60% strength dispersion of sodium hydride, which has previously been washed with petroleum ether, and 114.5 g of biphenylmethyl-triphenyl-phosphonium chloride in 450 ml of dimethylsulphoxide. After stirring for a further one hour, the reaction mixture is filtered, poured into 2,000 ml of ice-water and extracted with ether. The ether solution is washed with water, dried over sodium sulphate and evaporated. The residue is eluted on 1.0 kg of silica gel with methylene chloride-/ethyl acetate (1:1). After distilling off the methylene chloride/ethyl acetate mixture, 1,2-O-isopropylidene-3-O-benzyl-5,6-dideoxy-6-biphenyl-α-D-xylo-cis-hex-5-enofuranose of R$_f$=0.3 (thin layer chromatography on silica gel) in the system methylene chloride and an optical rotation $[\alpha]_D^{20} = -124° \pm 1°$ (c=0.746 in chloroform) is obtained and this is further processed without further purification.

A solution of 27.4 g of 1,2-O-isopropylidene-3-O-benzyl-5,6-dideoxy-6-C-biphenyl-α-D-xylo-cis-hex-5-enofuranose and 10.9 g of tetrabutylammonium bromide in 530 ml of chloroform is poured into a stirred solution, cooled to 0° C., of 260 g of sodium hydroxide pellets in 530 ml of water and the mixture is allowed to react for 20 hours at room temperature. 1,000 ml of methylene chloride are added to the resulting emulsion and the aqueous phase is separated off. The organic phase is washed with ice-cold 2 N hydrochloric acid and with water until neutral, dried over magnesium sulphate and filtered. The residue obtained after evaporating the filtrate is eluted with methylene chloride by column chromatography on 1.2 kg of silica gel. The product of R$_f$=0.50 (thin layer chromatography on silica gel) in the system methylene chloride and an optical rotation $[\alpha]_D^{20} = -60° \pm 1°$ (c=0.856 in chloroform) is pure 1,2-O-isopropylidene-3-O-benzyl-4-C-(cis-2,2-dichloro-3-biphenyl-cyclopropyl-1)-α-D-xylo-tetrofuranose in the form of slightly yellowish oil.

EXAMPLE 26

A solution of 22.0 g of 1,2-O-isopropylidene-3-O-benzyl-4-C-(2-S-phenyl-cyclopropyl-1-R)-α-D-xylo-tetrofuranose in 800 ml of a 0.2 N solution of methanesulphonic acid in ethyl alcohol is left to stand for 40 hours at room temperature. About 300 ml of ethanol are then distilled off and the methanesulphonic acid is neutralised with triethylamine. The reaction mixture is now completely freed from ethanol. The resulting residue is dissolved in ether, the solution is washed with water until neutral, dried over magnesium sulphate and filtered and the filtrate is evaporated. After crystallising the residue from methylene chloride/hexane (1:5), pure ethyl 3-O-benzyl-4-C-(2-S-phenyl-cyclopropyl-1-R)-D-xylo-tetrafuranoside is obtained in the form of white crystals with a melting point of 61°-68° (mixture of anomers) and an optical rotation $[\alpha]_D^{20} = -45° \pm 1°$ (c=1.107 in chloroform).

The starting material can be prepared as follows:

A solution of 348 g of 1,2-O-isopropylidene-3-O-benzyl-α-D-glucofuranose and 180 g of tetrabutylammonium bromide in 1,050 ml of methylene chloride is added to an ice-cooled solution of 264 g of sodium metaperiodate in 2,000 ml of water, with stirring, at a rate such that the temperature does not exceed 25° C. The mixture is allowed to react at room temperature for 4 hours, the aqueous phase is separated off and the methylene chloride phase is washed with water. 530 g of benzyltriphenylphosphonium bromide are dissolved in the methylene chloride solution, which contains 1,2-O-isopropylidene-3-O-benzyl-5-aldehydo-α-D-xylopentafuranose, and 2,600 ml of 0.5 N sodium hydroxide solution are added at room temperature, with stirring, and the mixture is allowed to react for 16 hours. The aqueous phase is then separated off and the methylene chloride solution is washed with water until neutral. After evaporating the methylene chloride solution, the residue, which contains 1,2-O-isopropylidene-3-O-benzyl-5,6-dideoxy-6-C-phenyl-α-D-xylo-cis-hex-5-enofuranose, is dissolved in 1,000 ml of chloroform and the solution is added to 1,800 ml of 5 N aqueous sodium hydroxide solution, with stirring and ice-cooling. The mixture is allowed to react at room temperature for 16 hours, the aqueous phase is separated off and a further 1,800 ml of 5 N aqueous sodium hydroxide solution are added to the chloroform phase. After allowing the mixture to react for a further 20 hours, the aqueous phase is separated off and the chloroform phase is washed with water until neutral. After evaporating the chloroform solution, pure 1,2-O-isopropylidene-3-O-benzyl-4-C-(2,2-dichloro-3-S-phenyl-cyclopropyl-1-R)-α-D-xylo-tetrofuranose crystallises from methanol in the form of white crystals with a melting point of 70° and an optical rotation $[\alpha]_D^{20} = -57° \pm 1°$ (c=1.552 in chloroform).

19.5 g of finely shredded lithium metal are added to a solution, cooled to −15°, of 117 g of 1,2-O-isopropylidene-3-O-benzyl-4-C-(2,2-dichloro-3-S-phenyl-cyclopropyl- 1-R)-α-D-xylotetrofuranose in 780 ml of tertiary butanol and 1,000 ml of absolute tetrahydrofurane in a nitrogen atmosphere. The reaction mixture is allowed to react at about −15° for 4 hours and is filtered and the filtrate is neutralised with 2 N ice-cold hydrochloric acid and evaporated to dryness. The residue is extracted with 120 ml of methylene chloride. After adding hexane to the methylene chloride solution, pure 1,2-O-isopropylidene-4-C-(2-S-phenyl-cyclopropyl-1-R)-α-D-xylo-tetrofuranose crystallises out in the form of white crystals with a melting point of 113°-113.5° C. and an optical rotation $[\alpha]_D^{20} = -87° \pm 1°$ (c=1.265 in chloroform).

340 ml of 1 N sodium hydroxide solution are added to a solution of 23.4 g of 1,2-O-isopropylidene-4-C-(2-S-phenylcyclopropyl-1-R)-α-D-xylo-tetrofuranose, 29.0 ml of benzyl chloride and 27.3 g of tetrabutylammonium bromide in 170 ml of methylene chloride, with stirring, at room temperature, and the mixture is allowed to react for 24 hours. The aqueous phase is then separated off and the organic phase is washed with water until neutral. After drying over magnesium sulphate, the organic phase is filtered and the filtrate is evaporated. The residue is extracted with ether and the ether solution is washed with water. The ether solution, which has been dried over magnesium sulphate and filtered, is evaporated. Crystallisation of the residue gives pure 1,2-O-isopropylidene-3-O-isopropylidene-3-O-benzyl-4-C-(2-S-phenyl-cyclopropyl-1-R)-α-D-xylo-tetrofuranose with a $R_f=0.18$, thin layer chromatography on silica gel, in the system methylene chloride and an optical rotation $[\alpha]_D^{20} = -138°$ (c=1.038 in chloroform).

EXAMPLE 27

6.45 g of 1,2-O-isopropylidene-3-O-benzyl-4-C-(cis-2-phenyl-cyclopropyl-1)-α-L-arabinotetrofuranose dissolved in 600 ml of a 0.2 N solution of methanesulphonic acid in ethyl alcohol are allowed to react for 15 hours at room temperature with the exclusion of light and moisture. After cooling to 0° C., the reaction solution is neutralised with triethylamine and the bulk of the ethanol is distilled off under reduced pressure. The residue is extracted with ether and the ether solution is washed with water, dried over magnesium sulphate and filtered and the filtrate is evaporated. After degassing the residue under a high vacuum, this gives pure ethyl 3-O-benzyl-4-C-(cis-2-phenyl-cyclopropyl-1)-L-arabinotetrofuranoside with an optical rotation $[\alpha]_D^{20} = +12° \pm 1°$ (c=1.530 in chloroform) and $R_f=0.56$ for the β-anomer and $R_f=0.26$ for the α-anomer.

The starting material can be prepared as follows:

A solution of 130 g of 1,2-O-isopropylidene-3-O-benzyl-5,6-dideoxy-6-S-phenyl-α-D-xylo-cis-hex-5-enofuranose and 46.7 g of tetrabutylammonium bromide in 1,240 ml of chloroform is added dropwise in the course of 45 minutes to 1,240 ml of ice-cold 10 N aqueous sodium hydroxide solution, with stirring. The mixture is then allowed to react at room temperature for 16 hours and the aqueous phase is then separated off. The chloroform phase is washed with water until neutral, dried over magnesium sulphate and filtered and the filtrate is evaporated. The residue is purified by column chromatography on 3 kg of silica gel with methylene chloride. The product which has a Rf=0.57 (thin layer chromatography on silica gel) in the system methylene chloride is pure 1,2-O-isopropylidene-3-O-benzyl-4-C-(cis-2,2-dichloro-3-phenyl-cyclopropyl-1)-β-L-arabinotetrofuranose with an optical rotation $[\alpha]_D^{20} = -23° \pm 1°$ (c=1.275 in chloroform).

4.0 g of finely shredded lithium metal are added to a solution, cooled to −15° C., of 45.0 g of 1,2-O-isopropylidene-3-O-benzyl-4-C-(cis-2,2-dichloro-3-phenyl-cyclopropyl-1)-β-L-arabinotetrofuranose in 240 ml of tertiary butanol and 500 ml of absolute tetrahydrofurane in a nitrogen atmosphere. The mixture is then allowed to react for 12 hours at 0° C. The reaction mixture is filtered, the filtrate is evaporated to about 90 g and the residue is extracted with methylene chloride. The methylene chloride solution is washed with water until neutral, dried over magnesium sulphate and filtered and the filtrate is evaporated. After crystallising the residue from methylene chloride/hexane (1:5), this gives pure 1,2-O-isopropylidene-4-C-(cis-2-phenyl-cyclopropyl-1)-β-L-arabinotetrofuranose with a $R_f=0.34$ (thin layer chromatography on silica gel) in the system methylene chloride/ethyl acetate (85:15) and an optical rotation $[\alpha]_D^{20} = -47° \pm 1°$ (c=0.947 in chloroform).

A solution of 10.0 g of 1,2-O-isopropylidene-4-C-(cis-2-phenyl-cyclopropyl-1)-β-L-arabinotetrofuranose, 8.2 ml of benzyl chloride and 12.7 g of tetrabutylammonium bromide in 100 ml of methylene chloride is poured into 118 ml of 1 N sodium hydroxide solution, with stirring, and the mixture is allowed to react for 17 hours at room temperature. The aqueous phase is then separated off and the methylene chloride phase is evaporated. The resulting residue is extracted with n-hexane and the hexane solution is washed with water. After drying the hexane phase over magnesium sulphate, it is filtered and the filtrate is evaporated to dryness. The residue is crystallised from hexane and is pure 1,2-O-isopropylidene-3-O-benzyl-4-C-(cis-2-phenyl-cyclopropyl-1)-β-L-arabinofuranose with a $R_f = 0.19$ (thin layer chromatography) in the system methylene chloride, a melting point of 77°–78° C. and an optical rotation $[\alpha]_D^{20}$: $+35°\pm1°$ (c=1.621 in chloroform).

EXAMPLE 28

Capsules containing 0.1 g of the active ingredient can be prepared as follows (for 10,000 capsules):

| Composition: | |
|---|---|
| Ethyl 3-O-benzyl-5,6-dideoxy-6-phenyl-D-xylo-hex-5-enofuranoside | 1,000 g |
| Absolute ethanol | 100 g |

The ethyl 3-O-benzyl-5,6-dideoxy-6-phenyl-D-xylo-hex-5-enofuranoside is mixed with the ethanol and the mixture is filled into soft gelatin capsules with the aid of a suitable capsule machine.

What is claimed is:

1. A compound of the formula I

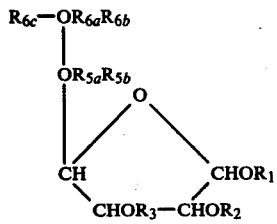

in which $R_1$ is lower alkyl or cycloalkyl having 5–8 carbon atoms and $R_2$ is hydrogen, lower alkyl or acyl, or $R_1$ and $R_2$ together are lower alkylidene or cycloalkylidene having 4 to 7 carbon atoms, $R_3$ is hydrogen, lower alkyl, lower alkenyl or aryl lower alkyl, $R_{5a}$ and $R_{6a}$ independently of one another are hydrogen or lower alkyl, $R_{5b}$ and $R_{6b}$ independently of one another are hydrogen, hydroxy, lower alkoxy, amino, lower alkylamino or diloweralkylamino or $R_{5b}$ and $R_{6b}$ together are a C-C bond, epoxy, lower alkylidene, or mono- or dihalogen-lower alkylidene and $R_{6c}$ is 1- or 2-naphthyl, diphenyl, phenyl, halogenophenyl trifluoromethyl-phenyl, lower alkyl-phenyl, lower alkoxy-phenyl, cyano-phenyl, nitro-phenyl, amino-phenyl, lower alkylamino-phenyl or dilower alkylaminophenyl.

2. A compound of the formula I according to claim 1, in which $R_1$ is lower alkyl, $R_2$ is an acyl radical of a carboxylic acid, $R_3$ is hydrogen, lower alkyl, lower alkenyl, benzyl, lower alkyl-benzyl, lower alkoxy-benzyl; halogenobenzyl or trifluoromethylbenzyl, $R_{5a}$ and $R_{6a}$ independently of one another are hydrogen, hydroxyl, or lower alkoxy or lower alkylamino, or $R_{5b}$ and $R_{6b}$ together are a C—C bond, epoxy, lower alkylidene or halogeno-lower alkylidene, and $R_{6c}$ is phenyl, halogenophenyl, trifluoromethylphenyl, lower alkylphenyl or lower alkoxyphenyl.

3. A compound of formula I according to claim 1, in which $R_1$ is lower alkyl, $R_2$ is an acyl radical of the formula

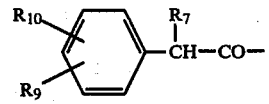

in which $R_7$ is hydrogen or lower alkyl, $R_9$ is hydrogen, halogen or trifluoromethyl and R is phenyl, cycloalkyl having 5–8 carbon atoms, 1-cycloalkenyl, or lower alkoxy, lower alkyl or 1-pyrrolyl and $R_3$, $R_{5a}$, $R_{6a}$, $R_{6b}$ and $R_{6c}$ are as defined in claim 1.

4. A compound of the formula I of claim 1 in which $R_{5b}$ and $R_{6b}$ together are a C—C bond and $R_1$, $R_2$, $R_3$, $R_{5a}$, $R_{6a}$ and $R_{6c}$ are as defined in claim 1.

5. A compound according to claim 1 in which $R_1$ is lower alkyl and $R_2$ is hydrogen, lower alkyl, lower alkanoyl, carboxy-lower alkanoyl or aroyl or $R_1$ and $R_2$ together are also lower alkylidene, $R_3$ is hydrogen, lower alkenyl, benzyl, lower alkyl-benzyl, lower alkoxy-benzyl, halogenobenzyl or trifluoromethylbenzyl, $R_{5a}$ and $R_{6a}$ independently of one another are hydrogen or lower alkyl and $R_{5b}$ and $R_{6b}$ independently of one another are hydrogen, hydroxyl, lower alkoxy or lower alkylamino, or $R_{5b}$ and $R_{6b}$ together are a C—C bond, epoxy, lower alkylidene or halogeno-lower alkylidene, and $R_{6c}$ is phenyl, halogenophenyl, trifluoromethylphenyl, lower alkylphenyl or lower alkoxy-phenyl or diphenyl.

6. A compound of the formula I of claim 5, in which $R_{5b}$ and $R_{6b}$ together are a C—C bond and $R_1$, $R_2$, $R_3$, $R_{5a}$, $R_{6a}$ and $R_{6c}$ are as defined in claim 5.

7. A compound according to claim 1 in which $R_1$ is lower alkyl and $R_2$ is hydrogen, lower alkyl, lower alkanoyl, carboxy-lower alkanoyl, benzoyl, halogenobenzoyl, trifluoromethylbenzoyl, lower alkyl-benzoyl, lower alkoxy-benzoyl, hydroxybenzoyl, lower alkanoyloxy-benzoyl or pyridylcarbonyl, or $R_1$ and $R_2$ are lower alkylidene, $R_3$ is hydrogen, lower alkyl, lower alkenyl, benzyl, lower alkyl-benzyl, lower alkoxy-benzyl, halogenobenzyl or trifluoromethylbenzyl, $R_{5a}$ and $R_{6a}$ independently of one another are hydrogen or lower alkyl and $R_{5b}$ and $R_{6b}$ independently of one another are hydrogen, hydroxyl, lower alkoxy or lower alkylamino, or $R_{5b}$ and $R_{6b}$ together are a C—C bond, epoxy, lower alkylidene or halogeno-lower alkylidene, and $R_{6c}$ is phenyl, halogenophenyl, trifluoromethylphenyl, lower alkyl-phenyl or lower alkoxy-phenyl or diphenyl.

8. A compound according to claim 1 in which $R_1$ is lower alkyl and $R_2$ is hydrogen, lower alkyl, lower alkanoyl, carboxy-lower alkanoyl, benzoyl, halogenobenzoyl, trifluoromethylbenzoyl, lower alkyl-benzoyl, lower alkoxy-benzoyl, hydroxybenzoyl, lower alkanoyloxy-benzoyl or pyridylcarbonyl, or $R_1$ and $R_2$ together are also lower alkylidene, $R_3$ is lower alkyl, benzyl, methylbenzyl, methoxybenzyl, chlorobenzyl, bromobenzyl or trifluoromethylbenzyl, $R_{5a}$ and $R_{6a}$ are hydrogen and $R_{5b}$ and $R_{6b}$ independently of one another are hydrogen, hydroxyl, lower alkoxy or lower alkylamino, or $R_{5b}$ and $R_{6b}$ together are a C—C bond, epoxy, methylene, chloromethylene, dichloromethylene, bromomethylene or dibromomethylene, and $R_{6c}$ is phenyl, chlorophenyl, bromophenyl, trifluoromethylphenyl, methylphenyl, methoxyphenyl or diphenyl.

9. A compound according to claim 1 in which $R_1$ is methyl, ethyl, n-propyl or n-butyl and $R_2$ is hydrogen, methyl, ethyl, n-propyl, n-butyl, lower alkanoyl having 2-4 C atoms, carboxy-lower alkanoyl having 2-4 C atoms, benzoyl, chlorobenzoyl, bromobenzoyl, methylbenzoyl, methoxy-benzoyl, hydroxybenzoyl, lower alkanoyloxy-benzoyl having 2-4 C atoms in the lower alkanoyloxy moiety, or pyridylcarbonyl, or $R_1$ and $R_2$ together are also iso-propylidene, $R_3$ is methyl, ethyl, n-propyl, n-butyl, benzyl, methylbenzyl, methoxybenzyl, chlorobenzyl, bromobenzyl or trifluoromethylbenzyl, $R_{5a}$ and $R_{6a}$ are hydrogen and $R_{5b}$ and $R_{6b}$ independently of one another are hydrogen, hydroxyl, methoxy or isopropylamino, or $R_{5b}$ and $R_{6b}$ together are a C—C bond, epoxy, methylene, chloromethylene or dichloromethylene, and $R_{6c}$ is phenyl, chlorophenyl, bromophenyl, trifluoromethylphenyl, methylphenyl, methoxyphenyl or diphenyl.

10. A compound according to claim 1 in which $R_1$ is methyl, ethyl, n-propyl or n-butyl and $R_2$ is hydrogen, methyl, ethyl, n-propyl, acetyl, propionyl, butyryl, benzoyl, chlorobenzoyl, hydroxybenzoyl, acetoxybenzoyl, propionyloxybenzoyl, butyryloxybenzoyl or pyridylcarbonyl, or $R_1$ and $R_2$ together are iso-propylidene, $R_3$ is methyl, ethyl, n-propyl, benzyl or chlorobenzyl, $R_{5a}$ and $R_{6a}$ are hydrogen and $R_{5b}$ and $R_{6b}$ independently of one another are hydrogen, hydroxyl, methoxy or isopropylamino, or $R_{5b}$ and $R_{6b}$ together are a C—C bond, epoxy, methylene, chloromethylene or dichloromethylene, and $R_{6c}$ is phenyl, chlorophenyl or diphenyl.

11. A compound according to claim 1 in which $R_1$ is methyl, ethyl, n-propyl or n-butyl and $R_2$ is hydrogen, methyl, ethyl, n-propyl, acetyl, propionyl, benzoyl, o-chlorobenzoyl, o-hydroxybenzoyl, o-acetoxybenzoyl, o-propionyloxybenzoyl or pyridylcarbonyl, or $R_1$ and $R_2$ together are iso-propylidene, $R_3$ is methyl, ethyl, n-propyl, benzyl or 4-chlorobenzyl, $R_{5a}$ and $R_{6a}$ are hydrogen, $R_{5b}$ and $R_{6b}$ together are a C—C bond and $R_{6c}$ is phenyl, 4-chlorophenyl or diphenyl.

12. The mixture of anomers of ethyl 3-O-benzyl-5,6-dideoxy-6-phenyl-D-xylohex-5-enofuranoside.

13. Ethyl 6-(4-chlorophenyl)-5,6-dideoxy-3-O-n-propyl-D-xylo-cis-hex-5-enofuranoside.

14. Ethyl 5,6-dideoxy-6-phenyl-3-O-n-propyl-D-xylo-cis-hex-5-enofuranoside.

15. n-Butyl 5,6-dideoxy-6-phenyl-3-O-n-propyl-D-xylo-cis-hex-5-enofuranoside.

16. n-Butyl-6-(4-chlorophenyl)-5,6-dideoxy-3-O-n-propyl-D-xylo-cis-hex-5-enofuranose.

17. n-Butyl-3-O-benzyl-5,6-dideoxy-6-phenyl-D-xylo-cis-hex-5-enofuranose.

18. Ethyl 3-O-benzyl-6-(4-chlorophenyl)-5,6-dideoxy-D-xylo-cis-hex-5-enofuranoside.

19. n-Butyl 3-O-benzyl-6-(4-chlorophenyl)-5,6-dideoxy-D-xylo-cis-hex-5-enofuranoside.

20. Ethyl 2-O-salicyloyl-6-(4-chlorophenyl)-5,6-dideoxy-3-O-n-propyl-D-xylo-cis-hex-5-enofuranoside.

21. Ethyl 2-O-acetyl-salicyloyl-6-(4-chlorophenyl)-5,6-dideoxy-3-O-n-propyl-D-xylo-cis-hex-5-enofuranoside.

22. Ethyl 3-O-n-propyl-5-deoxy-5-C-benzyl-D-xylofuranoside.

23. Ethyl 3-O-benzyl-4-C-(cis-2-phenyl-cyclopropyl-1)-α-D-xylo-tetrofuranoside.

24. Ethyl 3-O-benzyl-4-C-(cis-2-phenyl-cyclopropyl-1)-β-D-xylo-tetrofuranoside.

25. Ethyl 3-O-benzyl-4-C-(cis-2,2-dichloro-3-phenyl-cyclopropyl-1)-4-α-D-xylo-tetrofuranoside.

26. Ethyl 3-O-benzyl-4-C-(cis-2,2-dichloro-3-phenyl-cyclopropyl-1)-4-β-D-xylotetrofuranoside.

27. 1,2-O-Isopropylidene-3-O-benzyl-5,6-dideoxy-6-(4-methylphenyl)-α-D-xylo-cis-hex-5-enofuranose.

28. 1,2-O-Isopropylidene-3-O-benzyl-5,6-dideoxy-6-(4-methoxy-phenyl)-α-D-xylo-cis-hex-5-enofuranose.

29. 1,2-O-Isopropylidene-3-O-n-propyl-5,6-anhydro-6-C-phenyl-β-L-glycero-L-ido-hexafuranose.

30. 1,2-O-Isopropylidene-3-O-n-propyl-6-deoxy-6-isopropylamino-6-C-phenyl-β-L-idofuranose.

31. 1,2-O-Isopropylidene-3-O-benzyl-5,6-anhydro-6-C-(4-methylphenyl)-β-L-glycero-L-ido-hexafuranose.

32. 1,2-O-Isopropylidene-3-O-benzyl-5,6-dideoxy-6-C-phenyl-α-D-xylo-trans-hex-5-enofuranose.

33. Ethyl 3-O-benzyl-4-C-(trans-2-henyl-cyclopropyl-1)-α-D-xylo-tetrofuranoside.

34. Ethyl 3-O-benzyl-4-C-(trans-2-phenyl-cyclopropyl-1)-β-D-xylo-tetrofuranoside.

35. 1,2-O-Isopropylidene-3-O-benzyl-5,6-anhydro-6-C-phenyl-β-L-glycero-L-ido-hexofuranose.

36. 1,2-O-Isopropylidene-3-O-benzyl-4-C-(2-R-chloro-3-S-phenyl-cyclopropyl-1-R)-α-D-xylo-tetrofuranose.

37. Ethyl 3-O-n-propyl-4-C-(cis-2-phenyl-cyclopropyl-1)-D-xylo-tetrofuranoside.

38. 1,2-O-Isopropylidene-3-O-benzyl-4-C-(2-S-chloro-3-R-biphenyl-cyclopropyl-1-R)-α-D-xylo-tetrofuranose.

39. Ethyl 3-O-benzyl-4-C-(2-S-phenyl-cyclopropyl-1-R)-D-xylo-tetrafuranoside.

40. Ethyl 3-O-benzyl-4-C-(cis-2-phenyl-cyclopropyl-1)-L-arabino-tetrofuranoside.

41. An anti-inflammatory or an analgesic pharmaceutical composition which comprises a therapeutically effective amount of a compound of claim 1 together with a pharmaceutically acceptable carrier.

42. A method for the treatment of inflammation which comprises administeration of a therapeutical effective amount of a compound of claim 1.

* * * * *